United States Patent
Gonzalez-Lima

(10) Patent No.: US 6,183,981 B1
(45) Date of Patent: Feb. 6, 2001

(54) DIAGNOSTIC ASSAY FOR LATE-ONSET ALZHEIMER'S DISEASE

(75) Inventor: Francisco Gonzalez-Lima, Austin, TX (US)

(73) Assignee: Board of Regents, The University of Texas System, Austin, TX (US)

(*) Notice: Under 35 U.S.C. 154(b), the term of this patent shall be extended for 0 days.

(21) Appl. No.: 09/262,699

(22) Filed: Mar. 4, 1999

Related U.S. Application Data

(60) Provisional application No. 60/076,887, filed on Mar. 5, 1998.

(51) Int. Cl.[7] ............................. C12Q 1/26; C12Q 1/00; C12Q 33/53
(52) U.S. Cl. ................................. 435/25; 435/4; 435/975
(58) Field of Search .............................. 435/25, 4, 975

(56) References Cited

U.S. PATENT DOCUMENTS

| | | | |
|---|---|---|---|
| 4,965,074 | 10/1990 | Leeson | 436/518 |
| 5,545,566 | 8/1996 | Growden et al. | 435/7.1 |
| 5,565,323 | * 10/1996 | Parker et al. | 435/25 |
| 5,686,269 | 11/1997 | Nixon | 436/71 |
| 5,705,401 | 1/1998 | Masters et al. | 424/449 |

OTHER PUBLICATIONS

Davis et al, Proc. Natl. Acad. Sci, vol. 94, p 4526–4531, Apr. 1997. Month not available.*

Mattson, M.P., Trends Neurosci., vol. 20(9), p 373–375, 1997. Month not available.*

Bennett et al., "Cytochrome Oxidase Inhibition: A Novel Animal Model Of Alzheimer's Disease", *J. Geriatric Psych. Neurol.*, 5:93–101, 1992. Month not available.

Benzi et al., "Effect Of Chronic Treatment With Some Drugs On The Enzymatic Activities Of The Rat Brain", *Biochem. Pharmacol.*, 28:2703–2708, 1979. Month not available.

Cada et al., "Regional Brain Effects Of Sodium Azide Treatment On Cytochrome Oxidase Activity: A Quantitative Histochemical Study", *Metabolic Brain Disease*, 10:303–320, 1995. Month not available.

Chandrasekaran et al., Diffenential Expressions of Cytochrome Oxidase (COX) Genes in Different Regions of Monkey Brain, *J. Neuroscience Res.*, 32:415–423, 1992. Month not available.

Chieco et al., "A User's Guide For Avoiding Errors In Absorbance Image Cytometry: A Review With Original Experimental Observations," *Histochem. J.*, 26:1–19, 1994. Month not available.

Curti et al., "Age–Related Modifications Of Cytochrome C Oxidase Activity In Discrete Brain Regions," *Mech. Aging Dev.*, 55:171–180, 1990. Month not available.

Darriet et al., "Distribution Of Cytochrome Oxidase In Rat Brain: Studies With Diaminobenzidine Histochemistry In Vitro And [$^{14}$C]Cyanide Tissue Labeling In Vivo," *J. Cereb. Blood Flow Metabl.*, 6:8–14, 1986. Month not available.

Davis et al., "Mutations In Mitochondrial Cytochrome C Oxidase Genes Segregate With Late—Onset Alzheimer's Disease", *Proc. Nat'l. Acad. Sci.*, 94:4526–4531, 1997. Month not available.

de la Monte et al., "Increased Levels Of Neuronal Thread Protein In Cerebrospinal Fluid Of Patients With Alzheimer's Disease," *Annals Neurol.*, 32:733–742, 1992. Month not available.

(List continued on next page.)

Primary Examiner—Louise N Leary
(74) Attorney, Agent, or Firm—Fulbright & Jaworski

(57) ABSTRACT

The present invention provides a quantitative assay for early diagnosis of late-onset sporadic AD in living individuals using peripheral tissue biopsy. The assay may also be used for post-mortem diagnosis. More particularly, the invention relates to detecting changes in the level of mitochondrial cytochrome oxidase activity for diagnosing and monitoring AD.

20 Claims, 10 Drawing Sheets

OTHER PUBLICATIONS

De Olmos and Heimer, "Mapping Of Collateral Projections With The HRP–Method," *Neurosci. Lett.*, 6:107–114, 1977. Month not available.

Gonzalez–Lima and Cada, "Cytochrome Oxidase Activity In The Auditory System Of The Mouse: A Qualitative And Quantitative Histochemical Study," *Neuroscience*, 63:559–578, 1994. Month not available.

Gonzalez–Lima and Garrosa, "Quantitative Histochemistry Of Cytochrome Oxidase In Rat Brain", *Neurosci. Let.*, 123:251–253, 1991. Month not available.

Gonzalez–Lima and Gonzalez–Lima, "Sources Of Stress Affecting Caregivers Of Alzheimer's Disease Patients," *Health Values*, 11:3–10, 1987. Month not available.

Gonzalez–Lima and Jones, "Quantitative Mapping Of Cytochrome Oxidase Activity In The Central Auditory System Of The Gerbil: A Study With Calibrated Activity Standards And Metal–Intensified Histochemistry," *Brain Res.*, 660:34–49, 1994. Month not available.

Gonzalez–Lima et al., "Functional Mapping Of The Rat Brain During Drinking Behavior: A Fluorodeoxyglucose Study", *Physiol. Beh.*, 54:605–612, 1993. Month not available.

Gonzalez–Lima et al., "Quantitative Cytochemistry Of Cytochrome Oxidase And Cellular Morphometry Of The Human Inferior Colliculus In Control And Alzheimer's Patients", *Brain Res.*, 752:117–126, 1997. Month not available.

Gonzalez–Lima and Scheich, "Functional Activation In The Auditory System Of The Rat Produced By Arousing Reticular Stimulation: A 2–Deoxyglucose Study," *Brain Res.*, 299:201–214, 1984. Month not available.

Gonzalez–Lima, "Brain Imaging Of Auditory Learning Functions In Rats: Studies With Fluorodeoxyglucose Autoradiography And Cytochrome Oxidase Histochemistry," In: *Advances in Metabolic Mapping Techniques for Brain Imaging of Behavioral and Learning Functions*, NATO ASI Series D, vol. 68, Gonzalez–Lima, F., Finkenstaedt, Th., and Scheich, H. (Eds.), Kluwer Academic Publishers, Dordrecht/Boston/London, pp 39–109, 1992. Month not available.

Gonzalez–Lima et al., "Brain Cytochrome Oxidase Activity And How It Relates To The Pathophysiology Of Memory And Alzheimer's Disease," *Free Rdicles, Oxidative Stress and Antioxidants: Pathological and Physiological Significance, NATO ASI Series A*, 296:205–227, 1998. Month not available.

Hess and Pope, "Ultramicrospectrophotometric Determination Of Cytochrome Oxidase For Quantitative Histochemistry," *J. Biol. Chem.*, 204:295–306, 1953. Month not available.

Hevner et al., "An Optimized Method For Determining Cytochrome Oxidase Activity In Brain Tissue Homogenates," *J. Neurosci. Meth.*, 50:309–319, 1993. Month not available.

Jones et al., "Effects Of Intrauterine Position On The Metabolic Capacity Of The Hypothalamus Of Female Gerbils," *Physiol. Beh.*, 61:513–519, 1997. Month not available.

Kugler et al., "Cytochrome Oxidase Histochemistry In The Rat Hippocampus: A Quantitative Methodological Study," *Histochem.*, 89:269–275, 1988. Month not available.

Mecocci et al., "Oxidative Damage To Mitochondrial DNA Is Increased In Alzheimer's Disease," *Annals Neurol.*, 36:747–751, 1994. Month not available.

Nobrega et al, "Long–Term Changes In Regional Brain Cytochrome Oxidase Activity Induced By Electroconvulsive Treatment In Rats," *Brain Res.*, 605:1–8, 1993. Month not available.

Parker and Parks, "Cytochrome C Oxidase In Alzheimer's Disease Brain: Purification And Characterization," *Neurol.*, 45(3):482–486, 1995. Month not available.

Parker et al., "Cytochrome Oxidase Deficiency In Alzheimer's Disease," *Neurol.*, 40:1302–1303, 1990. Month not available.

Parker et al., "Reduced Platelet Cytochrome C Oxidase Activity In Alzheimer's Disease," *Neurol.*, 44:1086–1090, 1994a. Month not available.

Parker et al., "Electron Transport Chain Defects In Alzheimer's Disease Brain," *Neurol.*, 44:1090–1096, 1994b. Month not available.

Schagger and Ohm, "Human Diseases With Effects In Oxidative Phosphorylation. 2. $F_1F_0$ ATP–Synthase Defects In Alzheimer Disease Revealed By Blue Native Polyacrylamide Gel Electrophoresis," *Eur. J. Biochem.*, 227(3):916–21, 1995. Month not available.

Silverman and Tootell, "Modified Technique For Cytochrome Oxidase Histochemistry: Increased Staining Intensity And Compatibility With 2–Deoxyglucose Autoradiography," *J. Neurosci. Meth.*, 19:1–10, 1987. Month not available.

Van Raamsdonk et al., "Quantitative Cytochemical Analysis Of Cytochrome Oxidase And Succinate Dehydrogenase Activity In Spinal Neurons," *Acta Histochem.*, 81:129–141, 1987. Month not available.

Van Zuylen et al., "No Evidence For Reduced Thrombocyte Cytochrome Oxidase Activity In Alzheimer's Disease," *Neurol.*, 42:1246–1247, 1992. Month not available.

Waters, "Cognitive Enhancing Agents: Current Status In The Treatment Of Alzheimer's Disease," *Can. J. Neurol. Sci.*, 15:249–256, 1988. Month not available.

Wharton and Tzagoloff, "Cytochrome Oxidase From Beef Heart Mitochondria," *Meth. Enzymol.*, 10:245–250, 1967. Month not available.

de la Torre, J.C., "*Reduced cytochrome oxidase and memory dysfunction after chronic brain ioschemia in aged rats*", Neuro. Letters 223:165–168, 1997.

Simonian, Nacy A., "*Functional alterations in alzheimer's disease: diminution of cytochrome oxidase in the hippocampal formation*", J. of Neuropath. And Exper. Neurology, 52(6):580–585, 1993.

* cited by examiner

Brain

Muscle

Skin

Human Midbrain

DIAGNOSTIC ASSAY FOR LATE-ONSET ALZHEIMER'S DISEASE

The present application claims the priority of co-pending U.S. Provisional Patent Application Ser. No. 60/076,887, filed Mar. 5, 1998, the entire disclosure of which is incorporated herein by reference without disclaimer.

The government may own rights in the present invention pursuant to grant number RO1 MH43353 from the National Institutes of Health and grant number 003658-361 from the Advanced Technology Program, State of Texas.

BACKGROUND OF THE INVENTION

1. Field of the Invention

The present invention relates generally to the fields of pathology and diagnostics. More particularly, it concerns the early diagnosis of late-onset sporadic Alzheimer's Disease (AD). More specifically, the invention relates to detecting changes in the level of mitochondrial cytochrome oxidase for diagnosing and monitoring AD.

2. Description of Related Art

Alzheimer's Disease (AD) is characterized by initial memory loss, followed by progressive loss of neurons leading to dementia and loss of all nervous functions, and eventually death. AD is now the fourth-largest killer of adults 65 and older, and this disease impacts one of every three families in the United States (Gonzalez-Lima and Gonzalez-Lima, 1987), and affects over 13 million people world-wide. As the population trends lead to an increase in the number of older people, this figure will only increase.

AD may be categorized in one of two forms; familial AD or sporadic AD Familial AD accounts for only about 5% to 10% of all Alzheimer's cases and has an unusually early onset, generally before the age of fifty. Familial AD is inherited and follows conventional patterns of Mendelian inheritance. This form of AD has been linked to nuclear chromosomal abnormalities. In contrast, the second form of AD, sporadic AD, is a late-onset disease which is not inherited or caused by nuclear chromosomal abnormalities. This late-onset form of the disease is the more common type of AD and is believed to account for approximately 90 to 95% of all Alzheimer's cases. The cause of sporadic AD is not known.

Mitochondrial DNA defects are thought to be involved in a number of degenerative diseases, including Leber's hereditary optic neuropathy and myoclonic epilepsy lactic acidosis and stroke (MELAS). Such defects also are thought to involved in the "sporadic" (non-Mendelian) occurrence of neurodegenerative diseases such as Parkinson's and AD. Further, considering that the mitochondrion is the site of the electron transport pathway, it is not surprising that aberrant electron function has been described in both Parkinson's disease and AD. Cytochrome oxidase (CO, also known as ferrocytochrome c:oxygen oxidoreductase, cytochrome aa3, EC 1.9.3.1) is a key component of the mitochondrial electron transport chain, where it is responsible for the activation of oxygen for aerobic energy metabolism in all eukaryotic cells. CO is the terminal rate-limiting enzyme for cellular respiration. Since the brain relies almost exclusively on the aerobic metabolism of glucose for its energy, CO function is essential for normal brain function.

In recent years it has been reported that defects in cytochrome oxidase, may be involved in AD. Parker et al. (1990) showed that patients with AD have reduced cytochrome oxidase activity. Further, it has also been shown that when rats are infused with sodium azide, a specific inhibitor of cytochrome oxidase, the rats suffer from a form of behavior dysfunction characterized by impaired memory and learning (Bennett et al., 1992). These rats mimic the effect of AD in humans. In addition, the sodium azide-treated rats failed to display long-term potentiation, demonstrating loss of neuronal plasticity. Therefore, a chronic defect in CO activity in AD leads to oxidative damage to mitochondrial DNA and preferential cell death in the brain (Mecocci et. al., 1994).

The diagnosis of AD is by clinical observation and definitive diagnosis is only accomplished by pathological examination at autopsy. There have been many attempts to diagnose AD by identifying differences in biological markers such as protease nexin II and apolipoprotein E alleles, as well as monitoring cathepsin D in the patient's cerebrospinal fluid (U.S. Pat. No. 5,686,269), monitoring amyloid precursor protein (U.S. Pat. No. 5,705,401), and monitoring concentration of neuronal membrane phospholipids and phospholipid metabolites (U.S. Pat. No. 5,545,566). However, these approaches generally have a low rate of success or involve invasive techniques that are at best uncomfortable and often unreliable.

Additionally, measurement of increased levels of neuronal thread protein in cerebrospinal fluid of Alzheimer's patients has been proposed as a diagnostic test (de la Monte et al., 1992). Recently, this test has been available commercially as AD7C™ from NYMOX. It involves a lumbar puncture performed by a physician to obtain the cerebrospinal fluid. But AD7C™ has the disadvantage that it cannot be used as an early diagnostic test effectively because it relays on the increase in a protein resulting from neuronal degeneration. Therefore, significantly elevated levels of neuronal thread protein in cerebrospinal fluid can only be detected reliably after considerable irreversible neuronal death has occurred.

Because AD is progressive in nature, the efficiency of a cure could critically depend upon early detection. Additionally, the value of any new therapy could be better assessed if a rapid, safe and effective diagnostic procedure were available to monitor the progress of AD in patients following treatment. Therefore, there is a distinct need for a reliable, non-invasive, diagnostic laboratory test of AD so that this debilitating disorder may be detected at its earliest stages for efficient and effective intervention and treatment. The present invention is designed to address these needs.

SUMMARY OF THE INVENTION

In order to overcome deficiencies in the art, the present invention provides a quantitative assay for early diagnosis of late-onset sporadic Alzheimer's Disease (AD) in living individuals using peripheral tissue biopsy. The assay also may be used for postmortem diagnosis.

Thus, the present invention provides a method of diagnosing late-onset sporadic AD comprising the steps of obtaining a sample from a human subject; assessing cytochrome oxidase activity in nucleated cells of the sample; and comparing the cytochrome oxidase activity in nucleated cells of the sample with the cytochrome oxidase activity of a standard, wherein a decrease in cytochrome oxidase activity in nucleated cells of the sample, with respect to the standard, indicates that the subject has AD.

In preferred embodiments, the standard is cytochrome oxidase activity of like cells from an individual not afflicted with AD. In other preferred embodiments, the method further comprises assessing cytochrome oxidase activity from the like cells. In particularly preferred embodiments, the sample is a superficial tissue biopsy. In more defined embodiments, the biopsy is from a tissue selected from the group consisting of muscle, dermis, epidermis, bone marrow, peripheral ganglion or nerve. In certain preferred embodiments, the sample may be frozen and sectioned.

In particular aspects of the present invention, the assessing comprises providing diaminobenzidine (DAB) to cells of the sample and measuring oxidation of DAB to an indamine polymer. It is contemplated that measuring oxidation of DAB to an indamine polymer, when calibrated with spectrophotometry provides quantitative cytochemistry.

In particular embodiments, the cytochrome oxidase activity is quantified. In defined embodiments, the diagnostic cytochrome oxidase activity level of cells of the sample is significantly lower than the mean cytochrome oxidase activity level of the like cells. The term "significantly lower" as used herein is a cytochrome oxidase activity in the sample that is lower than the cytochrome oxidase in like cells. In preferred embodiments, the cytochrome oxidase activity is 10% or more below 15% or more below; 20% or more below; 25% or more below; 30% or more below; 35% or more below; 40% or more below; 45% or more below; 50% or more below; 55% or more below; 60% or more below; 65% or more below; 70% or more below; 75% or more below; 80% or more below; 85% or more below or 90% or more below the mean cytochrome oxidase activity level of the like cells.

Also contemplated by the present invention is a method for monitoring a treatment for late-onset sporadic AD comprising the steps of obtaining a sample from a human subject following a treatment thereof; assessing cytochrome oxidase activity in nucleated cells of the sample; and comparing the cytochrome oxidase activity in nucleated cells of the sample with a standard; wherein an increase in cytochrome oxidase activity in nucleated cells of the sample, with respect to the standard, indicates that the treatment is effective. In particular embodiments, the standard is cytochrome oxidase activity of like cells from the subject prior to the treatment. In more preferred embodiments, the standard is cytochrome oxidase activity of like cells from an individual not afflicted with AD. In other embodiments, the sample is a superficial tissue biopsy.

In certain aspects of the invention, it is contemplated that the assessing comprises providing diaminobenzidine (DAB) to cells of the sample and measuring oxidation of DAB to an indamine polymer. In more defined embodiments, measuring oxidation of DAB to an indamine polymer comprises quantitative cytochemistry when calibrated with spectrophotometry. In preferred embodiments, the sample may be frozen and sectioned.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: general appearance of the cytochrome oxidase (CO) stained human inferior colliculus (IC). It appears as a dark, ovoid structure oriented diagonally along the dorsal aspect of a transverse section through the midbrain. At most levels, it is clearly outlined by a ring of white matter: the incoming projections of the lateral lemniscus border the IC ventromedially and ventrolaterally, the commissure of the IC is present dorsomedially in rostral sections, and the brachium of the IC extends out along the dorsolateral surface. FIG. 1B: (Scanned images) the divisions with a Nissl stain. The IC can be subdivided into three nuclei: (1) Central nucleus (ICC): this nucleus is the largest of the three and contains the main projection fields of the lateral lemniscus. It makes up the entire ventromedial aspect of the IC, as outlined by the white matter of the lateral lemniscus. It is bordered dorsally and laterally by the other two nuclei. The ICC showed high metabolic activity (183.40±18.77 units). (2) Dorsal nucleus (ICD): this nucleus lies most dorsomedial just lateral to and making up portions of the commissure of the IC, This region showed high CO metabolic activity (184.98±45.08) which seems to correspond to its greater packing density of active neuropil. (3) External nucleus (ICE): the lateral border of the ICC is formed by the external nucleus. This nucleus can be viewed as a lighter band of gray matter extending along the lateral side of the ICC from ventro- to dorsolateral in a transverse section, bordered laterally by the lemniscus and brachium. This nucleus contained the lowest CO metabolic activity units (56.46±15.94). C: the distribution of large cells. The topographic distribution of CO deficits adjacent to the location of larger neurons in the ICC suggests hearing loss in AD involves both high and low tonotopic frequencies, CG, central gray. Scale bar equal for A, B, and C. Top is dorsal and right side is lateral.

FIG. 2B the same cell outlined for measurement as listed in the text. Averaged CO measurements are shown as borders; peak measurements are shown as boxes approximating the size of the sampled peak area. N, nucleus of cell. Scale bar equal for top and bottom figures.

FIG. 8A and FIG. 8B show rat brain regions measured. FIG. 8C and FIG. 8D show skeletal muscle, with clearly delineated red fibers (rich in mitochondrial enzymes) and white fibers (poor in mitochondrial enzymes). FIG. 8E and FIG. 8F show thin skin with cells in epidermis, dermis and smooth muscle fibers. FIG. 8G and FIG. 8H show higher magnifications of human nervous tissue from the midbrain, with well stained neuronal cell body characteristic of control subjects, from the study by Gonzalez-Lima et al. (1997).

DESCRIPTION OF ILLUSTRATIVE EMBODIMENTS

Figure 1A:
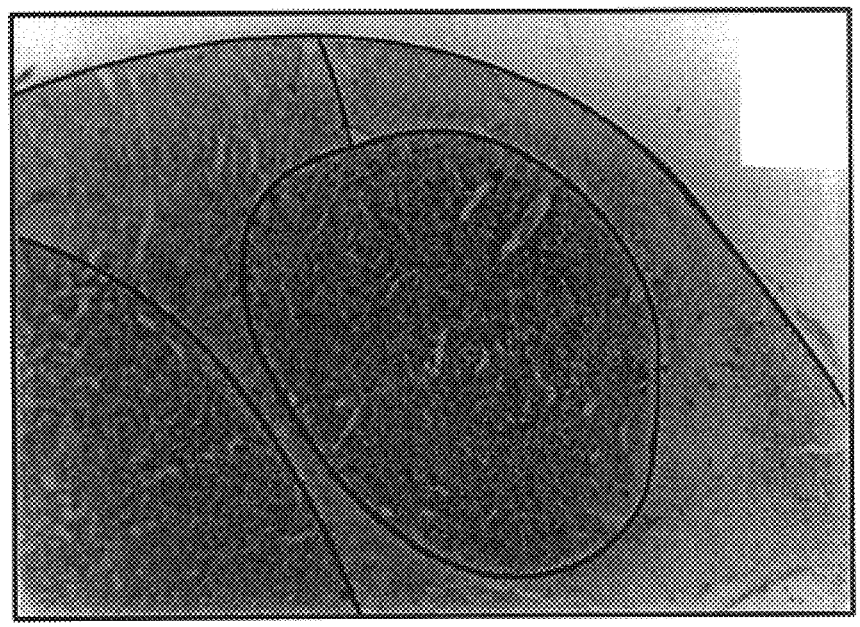
FIG. 1A, FIG. 1B, and FIG. 1C. The macroscopic inferior colliculus. (Scanned image)

Alzheimer's Disease is a debilitating neurodegenerative disease that is characterized by initial memory loss, followed by progressive loss of neurons leading to dementia and loss of all nervous functions, and eventually death. Sporadic late-onset AD accounts for 90%–95% of the total incidences of AD. Effectively, this disease can strike any individual over age 65, with little or no warning. Early diagnosis of this condition is imperative for halting the nervous tissue damage and ameliorating this debilitating condition. An indicator of the success of therapy is also necessary so that it can be determined whether a particular treatment regimen should be continued or abandoned.

It has been shown that cytochrome oxidase (CO) deficiency exists in the mitochondria of patients with AD (Parker et al., 1990). Subsequently, it has been shown that changes in cytochrome oxidase activity are indicative of AD. To date, the measurement of CO activity has required the use of neuronal tissue post-mortem, plateletpheresis and blood CO measurements. The diagnostic use of the assay used by Parker et al. (1990), is limited due to its complex plateletpheresis-based technique. This technique is not applicable to other peripheral tissues because it requires assays that were specifically developed for platelets, and which do not allow reliable measures of CO activity in other tissues. Simpler, more routine biochemical procedures for measuring CO activity in blood are too insensitive to detect the changes seen in AD patients (Van Zuylen et. al., 1992). Thus, the extent to which peripheral tissues provide reliable information is unknown. Moreover, because reliable diagnosis of AD requires the use of neuronal tissue, it has not been possible, thus far, to diagnose AD using peripheral tissues.

The present invention, for the first time, provides a simple, sensitive and reliable way of detecting AD in a living subject. The inventor has developed an assay that has the sensitivity to be a useful assay when employed in peripheral tissue, thereby ameliorating the need for neuronal or spinal cord tissue. Thus, in a preferred embodiment, the present invention provides an assay that can be used in peripheral tissues other than blood to provide a measure of the cellular CO activity. This assay can accurately quantify the CO activity of an individual using cytochemical procedures and automated image analysis.

1. Involvement of Cytochrome Oxidase in AD

Clinically, AD is characterized by progressive deficits in memory and other cognitive functions that occur in the face of an otherwise normal neurological examination. Postmortem examination reveals a variety of typical AD brain lesions, including deposition of amyloid plaques, formation of neurofibrillary tangles, and neuronal degeneration. The etiology and pathophysiology of neuronal death are unknown.

There is mounting evidence that a kinetic abnormality in CO is likely to be involved in the progression of AD. In biopsy samples from AD patients it has been shown that the electron transport chain is disrupted. It appears that the CO activity in brain and platelets of AD patients is decreased. Although there is a kinetic perturbation in the CO activity of AD patients, the concentration of CO present is normal (Parker and Parks, 1995; Schagger and Ohm, 1996). The activity of CO is decreased in the brain and peripheral tissue in late-onset AD. These results suggest that the biosynthesis of the CO complex occurs as normal, but that there is some catalytic defect. Other components of the electron transport chain appear to be normal in AD patients.

CO is encoded by the mitochondrial and the nuclear genome. However, the catalytic centers are exclusively encoded by two mitochrondrial genes. Davis et al., searched for mutation in the CO1, CO2 and CO3 genes (Davis et al., 1997). They showed that CO1 and CO2 genes contain specific missense mutations that may be maternally inherited. Cell lines exhibiting these mutations showed a specific decrease in CO activity and increased production of radical oxygen species. They concluded that point mutations in these two genes cause the CO defect in AD, and that this defect likely represents a primary etiological event that is directly involved in the cascade of events that culminated in clinical AD.

Cytochrome oxidase is an important terminal component of the electron transport chain located in the mitochondria of eukaryotic cells. Cytochrome oxidase, also known as complex IV of the electron transport chain, is composed of at least thirteen subunits. At least ten of these subunits are encoded in nuclear genes; the remaining three subunits (I, II, and III) are encoded by mitochondrial genes. Mitochondrial DNA (mtDNA) is a small circular DNA that is approximately 17 kB long in humans. The mtDNA encodes for two ribosomal RNAs (rRNA), a complete set of transfer RNAs (tRNA), and thirteen proteins, including the three cytochrome oxidase subunits COX I, COX II, and COX III.

2. Diagnostic Assay for AD

The present invention provides a cytochemical assay for the measurement of CO activity in individual cells. The assay is based on the use of calibrated tissue standards of known CO activity that are measured spectrophotometrically in conjunction with image microdensitometry at the light microscope level.

Metabolic mapping techniques often use calibrated standards. The problem of inter-assay variability largely can be resolved using a complete set of CO standards together with the tissue sections in each staining experiment. Thus, an internal calibration curve can be generated in each experiment, using the measured optical density of the standards and their spectrophotometrically determined CO activity units. This is the first quantitative cytochemical method which allows actual microdensitometric measures to be expressed as enzyme activity units.

Quantitative CO cytochemistry will be an appropriate mapping technique for the diagnosis, prognosis and postmortem analysis of human subjects suspected of AD. Mapped CO activity is theoretically related to other metabolic activity-based procedures such as fluorodeoxyglucose (FDG) autoradiography. This technique provides an ongoing index of regional brain glucose metabolism during and shortly after administration of an exogenous metabolic marker. However, CO is an endogenous respiratory enzyme which, when assessed cytochemically, can illustrate the effect of heightened or lessened metabolic demands on the individual tissue over an extended period of time. Thus, cytochemical examination of CO activity levels and thereby long-term neuronal activity patterns provide a method of quantifying cellular metabolic differences across groups of subjects and various pathophysiological states.

The cytochemical CO assay of the present invention is ideal for diagnosis and or prognosis of the pathophysiological manifestation of AD as well as monitoring the effects of therapy of such a state. In addition, the current assay can be used to follow the course of a neurodegenerative disease in an individual. Levels or ratios of CO activity are taken from the individual in a series of correlating samples over a period of time, in order to monitor changes in the values. The values from these samples are compared to the control samples described herein, to relate the values to those of other individuals with the disease, and thereby determine the severity of disease.

As stated above, the method also can be used to assess the efficacy of a drug for the treatment of AD. Levels of CO activity in samples taken from an individual before the administration of the drug are compared to levels in a corresponding sample taken from the individual after administration of the drug. These values further are compared to those of the control samples described herein. Efficacy of the drug is demonstrated if the levels of CO activity after drug administration are closer to AD negative (ie. increased from the diseased states) values than the levels before drug administration.

The sample subjected to analysis can be selected from any biological tissue that possesses CO activity. It is understood that the present cytochemical assay may be used on peripheral biopsy samples such as samples from muscle, dermis, epidermis, bone marrow, peripheral ganglion or nerve.

Theoretical Model of the Cytochemical Reaction

Figure 7:
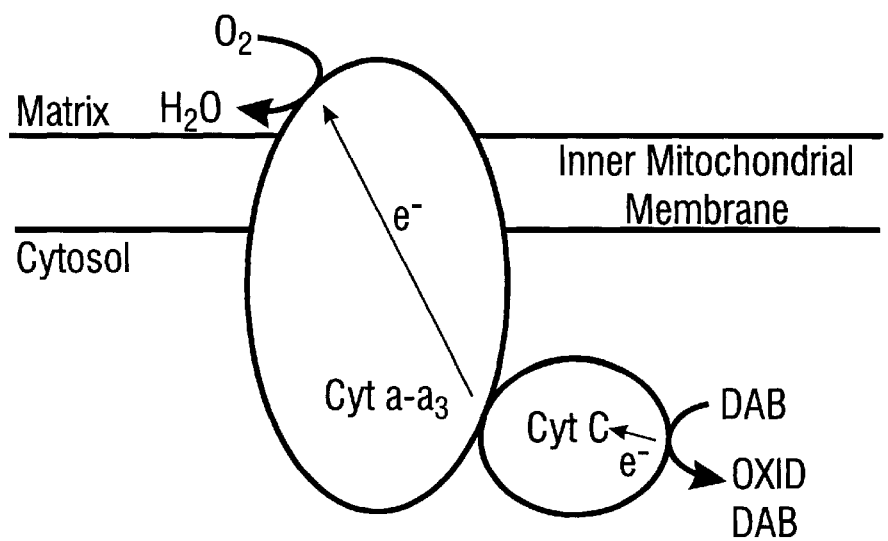
FIG. 7. Schematic of the model of the diaminobenzidine (DAB) cytochemical reaction adapted from Wong-Riley (1989) and Seligman et al. (1968). The staining in the cytochemical reaction is produced when DAB is oxidized to an indamine polymer (OXID DAB). Since continuous reoxidation of Cyt C by CO is required for the accumulation of the visible OXID DAB, this reaction serves to visualize CO activity.
Figure 8A:
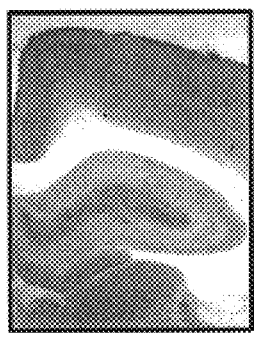
FIG. 8A, FIG. 8B, FIG. 8C, FIG. 8D, FIG. 8E, FIG. 8F, FIG. 8G and FIG. 8H. Scanned images of peripheral and brain tissues from rats and humans stained with the CO technique of the present invention. Lower and higher magnifications are shown in the left and right columns, respectively.
Figure 8B:
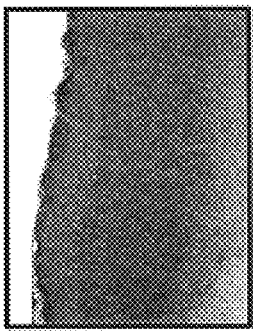
Figure 8C:
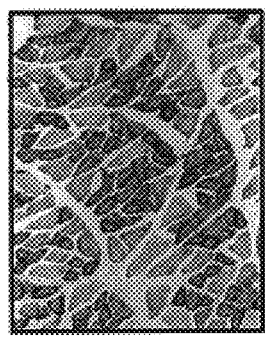
Figure 8D:
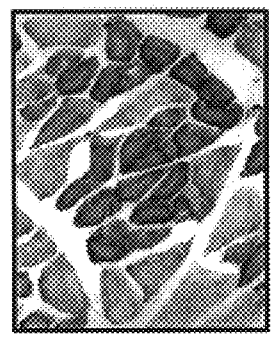
Figure 8E:
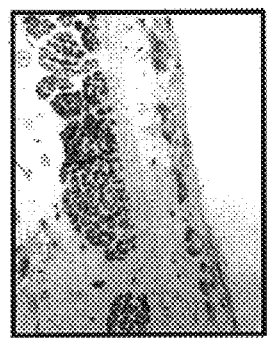
Figure 8F:
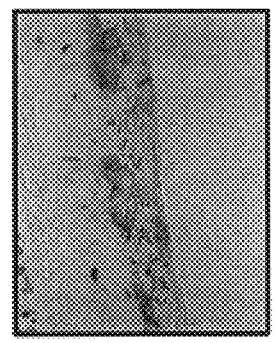
Figure 8G:
Figure 8H:
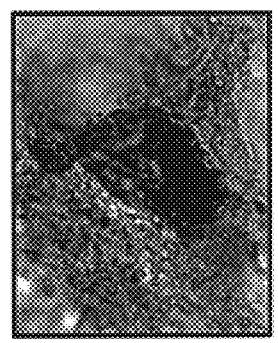

FIG. 7 is a schematic of the model of the diaminobenzidine (DAB) cytochemical reaction adapted from Wong-Riley (1989) and Seligman et al. (1968). CO is an integral transmembrane protein of the inner mitochondrial membrane. Electrons donated from DAB reduce cytochrome c (Cyt C). The heme units of CO (Cyt a-a3) catalyze the transfer of electrons from Cyt C to molecular oxygen to form water. The staining in the cytochemical reaction is produced when DAB is oxidized to an indamine polymer (OXID DAB). Since continuous reoxidation of Cyt C by CO is required for the accumulation of the visible OXID DAB, this reaction serves to visualize CO activity. The staining of the reaction product further is intensified by the addition of cobalt to the preincubation solution (Gonzalez-Lima and Jones, 1994).

The inventor's current quantitative CO method involves three steps. The first step is the preparation and spectrophotometric analysis of standards. This is followed by tissue sectioning and staining protocol that is compared with standards. The third step involves imaging of the stained tissue slides. These steps are described in detail herein below.

Preparation of Standards and Spectrophotometry

CO activity standards are made from the brains and peripheral tissues of a control animal, for example rat, monkey or even human. Tissues are homogenized at 4° C. and aliquots are frozen and sectioned at varying thickness to develop a gradient of CO activity in the sections to be used as standards. Standards are stained together with tissue sections to generate a calibration curve between standard CO activity and optical density in the tissue.

CO activity in the standards is spectrophotometrically measured with modified methods adapted from Wharton and Tzagoloff (1967), Hevner et al. (1993) and Cada et al. (1995), with modifications detailed below. Activity units were defined at pH 7 and 37° C. as 1 unit oxidizes 1 $\mu$mol of reduced cytochrome c per min ($\mu$mol/min/g tissue protein weight).

Detailed protocol:

This protocol describes the generation of a CO standard curve. CO standards are generated from the tissues of control animals. In specific embodiments, the tissues may be brain samples from control animals such as male rats. However, it is understood that the standard samples may be derived from any animal. The tissues are rapidly removed and stored in an appropriate buffer at 4° C., pH 7.4. The tissue is then homogenized at 4° C., divided into small aliquots, spun briefly in a 4° C. centrifuge to remove air, and frozen in −40° C.

To measure CO activity spectrophotometrically in the paste standards, a solution of 1.0% cytochrome c in potassium phosphate buffer (pH 7.0) is reduced with sodium ascorbate (indicated by a color change) (Cada et al., 1995, Gonzalez-Lima and Jones, 1994). Other small percent concentrations of cytochrome c also may be used but require recalibration with each kind of tissue used. The important point is to have excess cytochrome c so that the limiting factor in the reaction is CO activity. Other reducing agents, such as sodium hydrosulfite, may be used instead of sodium ascorbate. The excess reducing agent is removed by dialysis against potassium phosphate buffer for 24 h (three changes) at 4° C. This working concentration of cytochrome c is about 0.07% cytochrome c in 0.05 M potassium phosphate buffer.

The tissue homogenate is suspended in isolation buffer and chilled on ice. In preferred embodiments, approximately 1 g of tissue paste is suspended in 4 ml isolation buffer. The assay mixture contains final concentrations of 0.25% (w/v) tissue and 0.5% (w/v) sodium deoxycholate. For the assay, an aliquot of the assay mixture and an aliquot of the working concentration of cytochrome c are reacted together at 37° C. In order to monitor the CO activity, the change in absorbance at 550 nm is monitored. Activity units are defined at pH 7 and 37° C. as in the inventor's original quantitative method (Gonzalez-Lima and Garrosa, 1991) wherein 1 unit of CO oxidizes 1 $\mu$mol of reduced cytochrome c per min ($\mu$mol/min/g tissue wet weight).

Tissue Sectioning and Staining

Frozen tissue are sectioned at 40 $\mu$m and picked up on clean slides in a Frigocut 2800 cryostat at −15° C. Slides are processed for CO quantitative cytochemistry similarly as described in Cada et al. (1995) with modifications detailed below. Preincubation solution is followed by incubation at 37° C. for 60 min.

In preferred embodiments, slides may be treated to facilitate adherence of the tissue sections and standards to the slides. The tissue section may be washed with appropriate buffers. A preincubation step is included in which the slide is placed in cobalt chloride or another metal salt, to intensify tissue staining. The following is a detailed protocol for the materials and methods used in the staining procedure.

Detailed Protocol

Preferred Materials

1) Phosphate buffer from stock solutions (0.1 M monobasic and dibasic) in a ratio of 100 ml monobasic to 900 ml dibasic, and adjusted until pH 7.4.

2) Tris buffer is a mixture of 500 ml 0.2M Tris base, 774 ml 0.1N HCl and H2O to 2 l. To this add 550 mg cobalt chloride, 200 g sucrose and 10 ml DMSO. The phosphate and Tris buffers can be kept refrigerated for several days if color does not change.

3) The DAB solution for a 100 ml bath is made with 50 mg DAB (3,3'-diaminobenzidine tetrahydrochloride, Sigma), 7.5 mg cytochrome c (from horse heart, 95% minimum purity, prepared using TCA, Sigma), 5 g sucrose, 2 mg catalase (from bovine liver, 2,000–5,000 units activity/mg protein, Sigma), 0.25 ml DMSO, and phosphate buffer added to make 100 ml. The DAB incubation solution must be made fresh each time. Both the preincubation and incubation solutions must be renewed after each rack of slides is run through them.

4) The staining baths can be done conveniently in large glass staining dishes with a rack of slides. This is important to try to stain the same regions for sample and controls in a single incubation to minimize inter-staining variation.

5) Two or more complete sets of CO standards should be stained in each incubation bath.

Preferred Procedure

Sections should be kept frozen until placing in the sequence of baths and times listed below.

1) Cold buffered 0.5% glutaraldehyde in 0.1 M pH 7.4 phosphate buffer (4° C.) to affix sections, 5 min.

2) 0.1 M phosphate buffer with 10% sucrose (in four changes), 5 min each

3) Preincubation with Tris buffer and additives, 10 min 4) 0.1 M phosphate buffer rinse 5) Incubation with DAB solution (preceded by 5 min of oxygen bubbling) at 37° C. with automatic stirring in a dark oven, 120 min Diaminobenzidine and cytochrome c are essential to the reaction. Sucrose facilitates protection of cell membranes. DMSO is presumed to involve enhancing penetration of the reagents into the cells (DeOlmos and Heimer, 1977). DMSO can be added during the preincubation phase with favorable results. But these additives are effective only in the preincubation step (i.e., before the CO incubation reaction). Addition to the incubation reaction medium of DMSO (Kugler et al., 1988), and cobalt (Nobrega, 1992) offers little gains. Furthermore, metal intensification during incubation affects conditions necessary for quantification of CO activity. Catalase may be omitted without much deleterious effects. Catalase is a heme-containing protein that catalyzes the dismutation of hydrogen peroxide into water and molecular oxygen. Hydrogen peroxide is a normal product of oxygen respiration; thus the breakdown of these molecules has a two-fold advantage of preventing both interference by the free-radical in enzyme activity as well as the addition of molecular oxygen to the substrate.

With 40 micron sections, the reaction is conducted in a closed oven at 37° C. (measured inside the incubation solution) for 60–120 min for optimal quantitative results in human tissues. To stop the reaction and fix the tissue, slides are immersed in a buffer containing 4% formalin (v/v). The fixed samples are then dehydrated, cleared using for example xylene, and coverslipped with Permount.

Microscopic Image Analysis

Stained tissue slides were mounted on an light microscope connected to an imaging system. A high resolution CCD video camera mounted on the microscope is used to capture the images and transmit them to a frame grabber in a computer where the image is digitized. Analysis is completed with Jandel Scientific imaging software.

Detailed Protocol

Stained tissue slides are mounted on an Olympus light microscope (model BX40) connected to an image processing system. The same microscope lamp intensity level is set and verified densitometrically throughout the study, and condenser centration is performed prior to each imaging session to ensure that illumination levels are equivalent for the measurement of optical density.

A high resolution CCD video camera (Javelin JE-7442) is mounted on the microscope to capture the images and transmit them to a frame grabber (Targa M8) mounted in a computer where the image is digitized. Analysis is completed through the use of imaging software.

The recommendations of Chieco et al. (1994) are followed to avoid photometric errors in image cytometry. These recommendations are listed herein as follows. A clear background from a mounted slide is subtracted from each image to correct for lens and camera anomalies and shading distortion. An interference glass filter is interposed in the microscope light path to correct for white light distortion. The brightest pixel of the image is maintained a few gray levels below saturation to correct for blooming caused by excessive light. On the video camera, the automatic gain is switched off and the gamma control switched on to obtain gray levels linear with transmission. A 40× objective is used and sections stained lightly to avoid distributional error, glare, and diffraction errors. Pixel spacing may be calibrated with a stage micrometer separately for vertical and horizontal dimensions.

For spatial calibration, the JAVA software may be used in the computer to load conversion values into comparison tables. A calibration strip containing various gray levels of known optical densities (Kodak) can be imaged at the beginning of each session and used to construct a calibration curve for the conversion of gray levels to optical density for that session. Each imaging session is thus independently calibrated to optical density.

3. Definition of CO Activity Units

Besides differences in the preincubation and incubation histochemical protocols, there are factors such as temperature and pH related to the conditions used during biochemical enzymatic determination and the calculation of CO activity units. These relevant factors, however, are usually not all reported in previous enzymatic activity studies (Benzi et al., 1979; Curti et al., 1990; Darriet et al., 1986; Hess and Pope, 1953; Van Raamsdonk et al., 1987) making comparisons of absolute activity units complicated. The temperature of the reaction medium, for instance, would influence the speed of CO reaction product formation and calculated rate of activity.

The inventor has reported CO units measured spectrophotometrically at both 22° C. (standard room temperature) (Gonzalez-Lima and Cada, 1994) as well as at 37° C. (Gonzalez-Lima and Garrosa, 1991; Cada et al., 1995). For routine measures, solutions at 22° C. are more stable; that is, they show little auto-oxidation as compared to 37° C., which facilitates reproducibility of multiple triplicate assays from the same stock solutions. While Hess and Pope (1953) also have measured activity at 22° C., they have converted activity to 37° C. by multiplying units by a factor of 3, assuming CO activity to be doubled per each 10° C. rise in temperature. The inventor has not found this assumption to be valid. The definition of CO activity units using optimal reaction conditions for spectrophotometry, such as pH 7 at 37° C., may be preferable for studies evaluating absolute CO activity, rather than simpler routine assays (Hess and Pope, 1953) done at room temperature in which CO units can be defined reliably but at below maximal levels (Gonzalez-Lima and Cada, 1994).

An ideal situation is for all investigators to use the same conditions to define a unit of activity, and to consistently report data under these conditions. Alternatively, the activity from a whole-brain homogenate or a similar reference may be reported to provide a relative index of the enzymatic activity obtained under different measurement conditions. For example, homogenates of fresh-frozen rat brains showed an average CO activity of 175 units ($\mu$mol/min/g tissue w/w) in the assay conditions reported below. This average CO activity units in the control brains was very similar to the average CO activity in the whole rat brain (158±5) reported by Hevner et al., (1993). The present somewhat higher value may be attributed to the fact that the CO units herein were defined at pH 7 and 37° C., as in the original method (Gonzalez-Lima and Garrosa, 1991), as opposed to pH 6 and 30° C. as done by Hevner et al. (1993). The agreement between these control brain CO values suggests that both assays were optimal in unmasking enzyme activity to maximal or near maximal levels (Hevner et al., 1993). Whether the units are defined based on tissue wet weight (w/w) or dry weight needs also to be specified (Nobrega et al., 1993). The present activity units showed good agreement with values reported in the literature when similar conditions were used to measure and define the units of CO activity.

For those interested in reporting a relative CO quantification, without measurement of enzyme activity units, comparisons using relative indexes such as whole-brain or white matter as references may be useful. Reporting relative densitometric ratios, such as is done in 2-DG studies (e.g., Gonzalez-Lima and Scheich, 1984) is a useful approach that may suffice for many CO applications (e.g., Jones et al., 1997). It is valid to quantify relative values, as long as one does not presume that they represent absolute values. However, it should be cautioned that if a CO histochemical procedure fails to meet the quantitative requirements of linearity of reaction product formation with respect to incubation time and section thickness, it can not be used as a valid quantitative method with relative measures (Stoward, 1980).

Preincubation Metal Intensification with Tris Buffer and DMSO

Metal intensification with cobalt chloride, nickel ammonium sulfate or manganese chloride has been shown to enhance the sensitivity of detecting benzidine reaction products in HRP histochemistry (Adams, 1977; DeOlmos and Heimer, 1977). Ten min with a preincubation solution of 0.05M Tris buffer at pH 7.6, containing cobalt chloride and DMSO similar to that of Adams (1977) and DeOlmos and Heimer (1977), has increased the sensitivity of CO histochemistry over that of Wong-Riley's (1979) protocol without loss of specificity (Silverman and Tootell, 1987). The inventor confirmed this enhanced sensitivity in CO staining of rat brains when incorporating this preincubation step in the inventor's original quantitative histochemical procedure (Gonzalez-Lima and Garrosa, 1991).

The positive action of preincubation with cobalt chloride is seen in the formation of a darker reaction product, which may involve polymerization of the initial DAB reaction catalyzed by cobalt chloride. Excess precipitate is eliminated by repeated changes in phosphate buffer to remove the cobalt salts not incorporated into the mitochondrial reaction product (Silverman and Tootell, 1987). The inventor has repeatedly confirmed this cobalt-enhanced sensitivity and specificity in the CO staining of tissues from many different species, including humans (Gonzalez-Lima et al., 1997).

The use of maximal metal intensification during the incubation reaction facilitates morphological visualization of reaction product in all neurons (Kageyama and Robertson, 1993; Liu et al., 1993). However, using metal intensification procedures during incubation invalidate the quantitative requirements of graded reaction product reactivity proportional to CO enzymatic activity. That is because maximal intensification results in saturation of reaction product formation and similar dark staining of cells with low and high CO activities. If the objective of the CO stain is to obtain a quantitative functional index of CO activity, rather than a morphological index with saturated staining, then metal intensification is better used as a preincubation step rather than during incubation. In this manner, the incubation reaction can proceed undisturbed using parameters that result in nonsaturated reaction product formation in a rate of reaction linear with respect to increasing incubation time. For the same reason, CO histochemical procedures which yield reaction rates different during the first min and subsequent period of incubation (e.g., Kugler et al., 1988) are also invalid for quantitative CO histochemistry.

Temperature, pH, Oxygenation and Duration of the CO Incubation Reaction

DeOlmos and Heimer (1977) were able to increase the sensitivity of HRP histochemistry by manipulating intrinsic factors of the incubation reaction such as pH and temperature. Silverman and Tootell (1987) similarly improved CO staining intensity by increasing pH, temperature, and adding oxygen to the incubation medium. The standard spectrophotometric assay of CO developed by Wharton and Tzagoloff (1967) uses pH 7 at 37° C. for optimal CO activity in vitro. Although pH 7 appears optimal for biochemical assays of CO activity in separated mitochondria in vitro, pH 7.6 improves the histochemical staining facilitating entry of the reagents by swelling of tissue mitochondria in situ (Silverman and Tootell, 1987). Higher temperatures also can accelerate the CO reaction, but when using internal activity standards in the present quantitative method, a 37° C. temperature showed the best linearity between densitometric measures of staining intensity and incubation time.

Silverman and Tootell (1987) also found that oxygen saturation of the incubation medium improved CO staining by increasing DAB oxidation to form the colored reaction product. However, the inventor has found that saturation is best done before the introduction of the rack of slides with the sections.

This is because oxygen bubbling during the reaction causes a differential distribution of bubbles in the solution that results in nonuniform staining of adjacent slides (Gonzalez-Lima, 1992). Gentle agitation with a stirrer bar throughout the reaction and ample circulation between, above, and below the slides prevents the formation of a staining gradient by circulating the oxygen and reagents thoroughly. Exposure of the reaction medium to intense light needs to be avoided because it may produce spontaneous DAB oxidation leading to nonspecific staining.

4. Kits

The present invention also relates to methods of identifying and quantitating AD in a tissue and kits for use therein. The kits of the present invention will provide all the components necessary for a CO assay of the present invention. In this aspect, the present invention contemplates diagnostic kits for the determination of CO activity in a tissue sample. Said kits will likely contain the active standards and staining agents used in the present invention.

The kits also may include reagents necessary for the preparation of samples for a cytochemical analysis. As such it is contemplated that all the reagents necessary for processing a tissue sample will be included in a kit of the present invention.

The kits of the invention will generally comprise one or more standard tissues having a defined CO activity. Preferably, the kits will comprise, in suitable container means, one or more standard tissues selected from the group consisting of muscle, dermis, epidermis, bone marrow, peripheral ganglion or nerve of a non-AD origin for comparison with biopsy samples that will be taken from AD individuals. Alternatively, the kits may have a preparation comprising cytochrome oxidase.

Preferred kits are those suitable for use in a microscopic cytochemical assay. Also included in the kits may be reagents and buffers to provide the necessary reaction mixture for the cytochemical assay.

The kits of the present invention, also may contain a panel of calibration strips containing various gray levels of known optical densities to be used to construct a calibration curve for the conversion of gray levels to optical density for each session.

In each case, the kits will preferably comprise distinct containers for each individual reagent and enzyme. Each biological agent will generally be suitable aliquoted in their respective containers.

The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

5. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Human Subjects

Frozen tissue samples were received from the Alzheimer's Disease Research Center Neuropathology Core at the University of Southern California School of Medicine and from the Brain Bank of the Michigan Alzheimer's Disease Research Center at the University of Michigan Medical Center.

Tissue samples were stored at $-40°$ C. until processing. The non-AD, non-demented control group consisted of 5 males and 3 females with a mean age of $79.6\pm3.1$ years, a mean post-mortem interval of $6.9\pm1.6$ h, and a mean brain weight of $1287.5\pm39.8$ g. Non-AD cases died of cardiorespiratory failures or cancer. The AD group consisted of 7 males and 1 female with a mean age of $78.3\pm2.9$ years, a mean post-mortem interval of $6.5\pm1.3$ h, and a mean brain weight of $1175.0\pm50.9$ g.

Patients' reports included years since diagnosis of AD dementia (mean=$8.6\pm1.1$ years) and confirmation of AD histopathology. Six AD patients died of cardiorespiratory failure, but a cause of death other than AD was unavailable for the other two. The available drug histories showed no neuroleptic use. Student's two-tailed t-tests demonstrated no significant differences between the control group and the AD group in age ($p>0.75$), post-mortem interval ($p>0.84$), and brain weight ($p>0.10$).

Tissue Processing

Human brain tissue was sectioned at 40 $\mu$m in the transverse plane and picked up on clean slides in a Frigo-cut 2800 cryostat at $-15°$ C. Slides were processed for CO quantitative cytochemistry as in our previously described histochemical procedures (Gonzalez-Lima, 1992; Gonzalez-Lima and Cada, 1994; Gonzalez-Lima and Garrosa, 1991; Gonzalez-Lima and Jones, 1994) which were based on similar staining procedures (Silverman and Tootell, 1987; Wong-Riley, 1979). Preincubation (Adams et al., 1977) was followed by incubation at $37°$ C. for 120 min. Adjacent sections were stained with Cresyl violet to delineate the cytoarchitecture of the IC.

Spectrophotometric Assessment of Cytochrome Oxidase Activity

CO activity standards were made from the brains of 12 adult male rats. Each animal was decapitated, its brain rapidly removed and stored in $4°$ C. sodium phosphate buffer (pH 7.4) until all 12 brains were collected. The brains were homogenized at $4°$ C. and aliquots were frozen in 1.5 ml microtubes and sectioned at varying thicknesses to develop a gradient of CO activity in the sections used as standards. Sections of the standards were stained together with the IC sections for the generation of a regression equation between standard CO activity and optical density in the tissue in each staining batch (Gonzalez-Lima and Jones, 1994).

CO enzyme activity in the standards was spectrophotometrically measured using a method adapted from Wharton and Tzagoloff (1967) and Hevner et al. (1993) as reported in Cada et al. (1995). Activity units were defined at pH 7 and $37°$ C. as in our original quantitative method (Gonzalez-Lima and Garrosa, 1991) where 1 unit oxidizes 1 $\mu$mol of reduced cytochrome c per min ($\mu$mol/min/g tissue wet weight). Activity units can also be expressed in terms of grams of protein content (Lowry et al., 1951) by multiplying the reported values by 10 since our brain standards contained an average of 10% protein (Gonzalez-Lima and Cada, 1994).

Microscopic Image Analysis

Stained tissue slides were mounted on an Olympus light microscope (model BX40) connected to an image processing system. The same microscope lamp intensity level was set and verified densitometrically throughout the study, and condenser centration was performed prior to each imaging session to ensure that illumination levels were equivalent for the measurement of optical density. A high resolution CCD video camera (Javelin JE-7442) was mounted on the microscope to capture the images and transmit them to a frame grabber (Targa M8) mounted in a 486 computer (Dell) where the image was digitized.

Analysis was completed through the use of JAVA (Jandel Scientific) imaging software as described elsewhere in the specification. The recommendations of Chieco et al. (1994) were followed to avoid photometric errors in image cytometry.

A calibration strip containing various gray levels of known optical densities (Kodak) was imaged at the beginning of each session and was used to construct a calibration curve for the conversion of gray levels to optical density for that session. Each imaging session was thereby independently calibrated to optical density. Thickness standards of known CO activity (measured spectrophotometrically) were included in each staining batch and were imaged on a DC-powered light box using JAVA as described previously (Gonzalez-Lima et al., 1993). The optical density and activity measurements of these standards were then used to construct a regression equation.

The change in optical density showed linear relationships with respect to tissue activity, section thickness, and incubation time in each of the three staining batches done (r=0.96, 0.97, and 0.97). Optical density measures of the IC sections were thereby independently converted to CO activity units using the calibration curves generated with the standards' optical density and activity units.

Figure 1B:
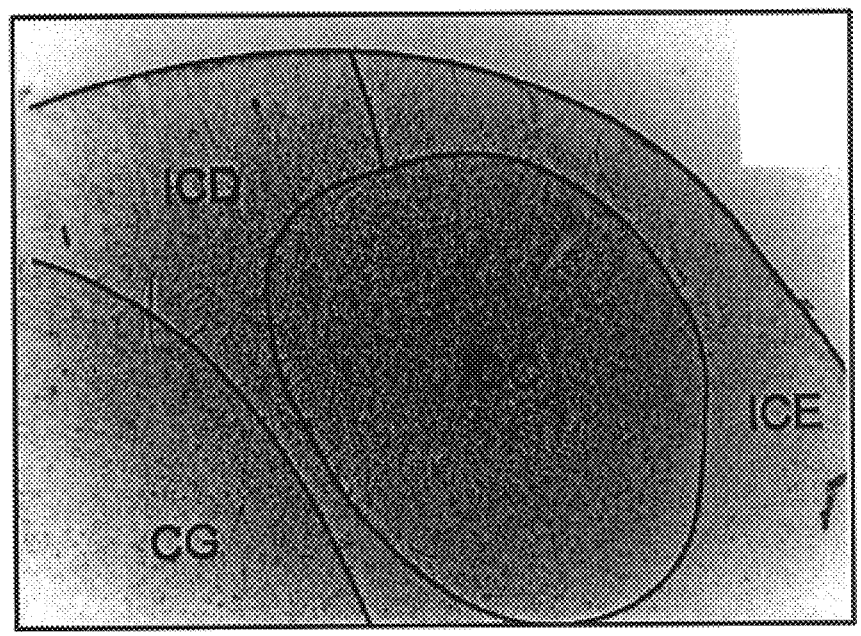

A total of 480 cells were sampled consisting of 30 cells per subject for 16 subjects. The inferior colliculus was subdivided into three separate nuclei: the central (ICC), dorsal (ICD) and external (ICE). To avoid mistakenly sampling from outside the intended nucleus, observations were restricted to the central part of the IC subdivisions, within the perimeters denoted in FIG. 1.

Figure 2A:
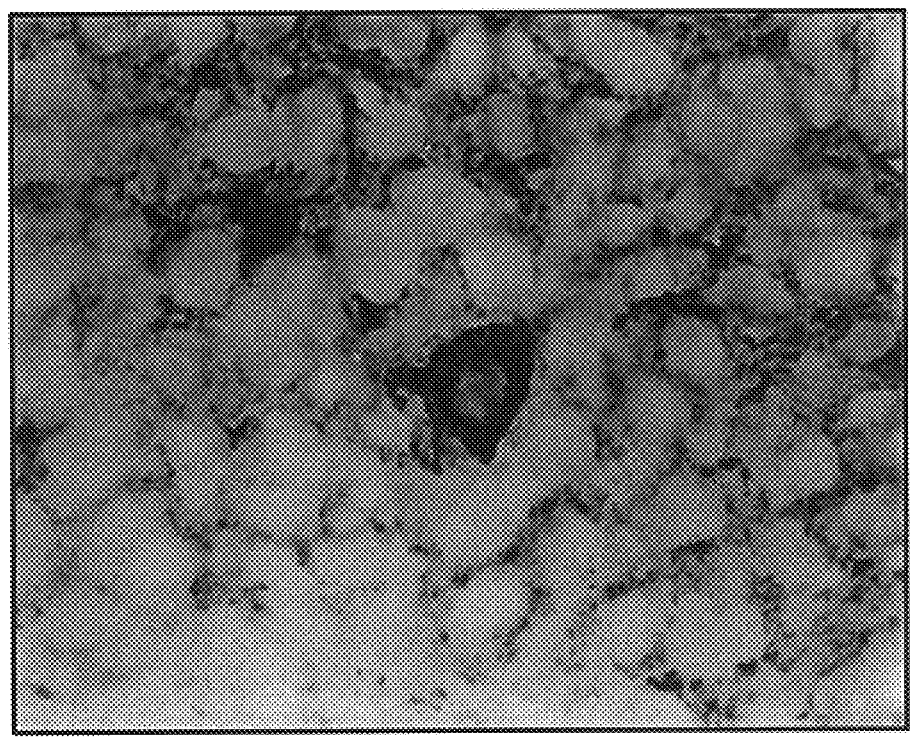
FIG. 2A and FIG. 2B. (Scanned images) FIG. 2A a large cell of the ICC, stained for CO.
Figure 2B:
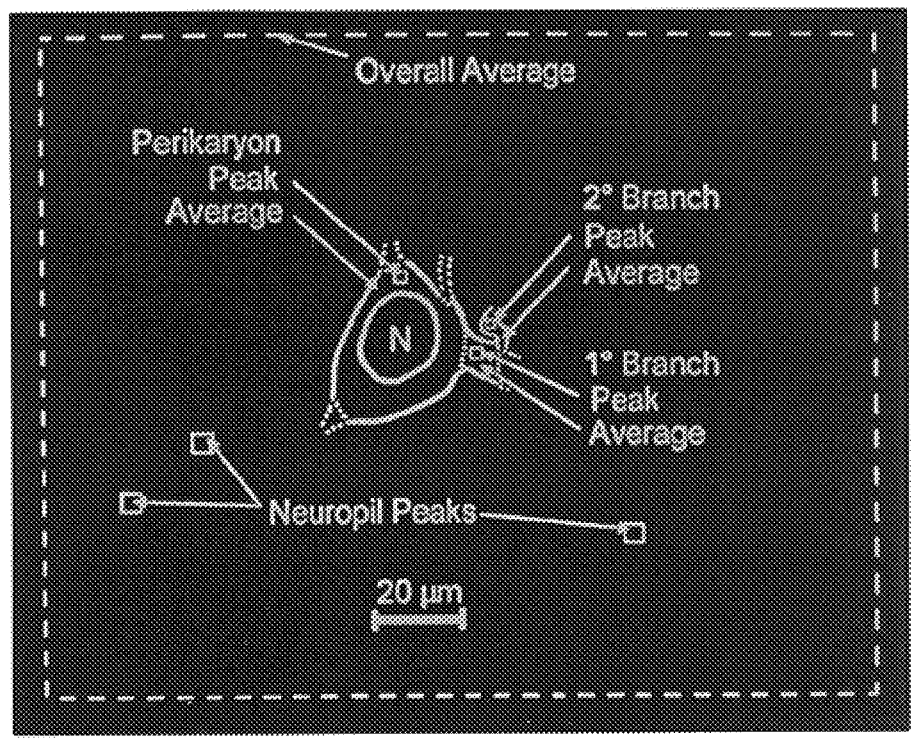

Ten cells were sampled randomly per nuclear subdivision per subject from up to 8 sections with sections sampled separated by at least a 120 $\mu$m interval. Additional selection criteria for sampling were that tissue was free from artifacts of staining and tissue processing (such as cracks, folds, and foreign particles) and that cells showed no obvious signs of morphological abnormalities (such as vacuolations, dendritic swellings, eccentric nuclei, etc.). All measurements were taken by a single observer. A total of 8 densitometric and 6 morphometric measures were taken from each cell; for these measurements the cell body was oriented in the center of the image area (FIG. 2). All measurements were taken using JAVA (Jandel) software, as follows:

Overall average: with the cell body in the center of the image area, the CO activity was averaged across the entire rectangular image area (165×130 $\mu$m). This area included primarily the neuropil that surrounded each single cell sampled, the cell body, and capillary space.

Neuropil peaks: the three highest points of peak activity in the neuropil of each rectangular image area of 165×130 $\mu$m were selected and measured. Each peak was measured by averaging an area contained within a 13×13 pixel (5×5 $\mu$m) window.

Perikaryon average: the average activity of the cell body, excluding the nucleus and any processes. This was measured by outlining the perimeter of the cell body and nucleus and averaging the interior of that outline.

Perikaryon peak: the point of highest activity in the perikaryon; the average of a 5×5 pixel (2.4×2.4 $\mu$m) window.

Primary branch peak: the point of highest activity in the primary branch of the largest arborizing process; the average of a 5×5 pixel window.

Primary branch average: the average activity of the above primary branch, measured by outlining the branch from the cell body to the first visible secondary branch and averaging the activity within.

Secondary branch peak: the point of highest activity in a secondary branch of the largest arborizing process; the average of a 3×3 pixel (1.7×1.7 $\mu$m) window.

Secondary branch average: the average activity of the above secondary branch, measured by outlining the branch from the primary branch to the first visible tertiary branch and averaging the activity within.

Soma diameter: diameter was measured perpendicular to the axis of the primary branch.

Soma area and perimeter: including the nucleus and excluding any processes; measured by outlining the cell body.

Nucleus diameter: again, measured perpendicular to the axis of the primary branch.

Nucleus area and perimeter: including only the nucleus of the cell; measured by outlining the nucleus of the cell.

EXAMPLE 2

Early Diagnosis of AD Using Deltoid Muscle Biopsy

A preferred method of monitoring AD in an individual is to detect CO activity inhibition in deltoid muscle biopsies as an early diagnostic aid in patients suspected of AD. A needle is inserted in the back of the shoulder with local anesthesia and a small (2 mm cubic) muscle sample is aspirated and processed for CO activity as described above.

Since the brain relies almost exclusively on the aerobic metabolism of glucose for its energy (Sokoloff, 1989), CO function is essential for normal brain function. But CO is the terminal rate-limiting enzyme for cellular respiration in all eukaryote cells, suggesting that a systemic CO deficiency may be detected in AD nonneural cells.

Therefore, the quantitative CO method can be applied in a laboratory biopsy assay for diagnosis of late-onset, sporadic AD in a peripheral tissue.

Skeletal muscle was studied first because of its rich supply of mitochondria and well-established use in diagnostic enzyme histochemistry of neuromuscular diseases (Bauserman and Heffner, 1984). Apolipoprotein E (ApoE)-epsilon 4 allele, associated with familial AD, has been found in skeletal muscle (Akaaboune et al., 1994). It has also been documented that CO reactivity decrements can be detected in muscle with routine histochemistry in some childhood genetic diseases caused by CO deficiencies that lead to neurodegeneration, such as Leigh's (subacute necrotizing encephalomyelopathy) and Alper's (progressive infantile poliodystrophy) diseases (Sarnat, 1983). So it is reasonable to assume that the inventor's more sensitive histochemical method used in older patients, with clinical manifestations of dementia, may serve as a differential diagnostic aid for sporadic AD. This could be done by confirming that the suspected patients have peripheral tissue CO activity decreases such as the 17% to 50% found in AD platelets (Parker et al., 1990, 1994a).

Samples from deltoid muscle are particularly well-suited to examine CO activity because they normally contain a predominance of Type I fibers. The two basic muscle fiber types in humans are Type I or red fibers and Type II or white fibers. The red fibers are primarily oxidative, while the white fibers are primarily glycolytic. As compared to white fibers, red fibers contain many more mitochondria and higher concentrations of oxidative enzymes (Sarnat, 1983). Thus, red fibers stain dark and white fibers stain light with the present CO histochemical method.

The inventor studied deltoid muscle samples from 12 subjects using quantitative CO histochemistry. Six of the subjects were late-onset AD cases with histopathologically confirmed AD, and the other six subjects were aged normal controls. There were four females and two males in each group. Their mean (± standard error) age was 83 (±2.4) and the postmortem time before freezing of the samples was 5±0.8 h.

There were no significant (p<0.05) group differences in age and postmortem time. But the groups showed clear significant differences in mean CO activity. The aged controls had 51.30±6.57 units of CO activity, whereas the AD subjects had 29.18±5.22 units. This corresponded to a significant (t-test, P=0.0249) mean decrease of 43% in the AD subjects.

Additionally, none of the AD cases showed CO activity values greater than the mean of the aged controls. These results suggest that muscle biopsy may be used as an early diagnostic aid in living subjects suspected of sporadic AD. An early diagnostic lab test of AD may facilitate a more effective medical treatment for the majority of AD cases, which are of the sporadic type. Monitoring of CO activity using muscle needle biopsies may also serve to evaluate the success of early treatments in reversing this enzymatic defect to prevent oxidative stress leading to neurodegeneration.

These data also support the hypothesis that sporadic AD is a systemic mitochondrial disease, characterized by CO inhibition. Furthermore, the finding of CO inhibition in peripheral tissues of AD patients has implications for the pathogenesis of AD. For example, it may be possible to argue that a decrease in CO activity observed in neurons is a nonspecific consequence of any neurological disease leading to cerebral hypometabolism.

However, a condition such as cerebral vascular changes, brain trauma, or other causative factors of brain hypometabolism are unlikely to explain a peripheral defect in CO activity as found in platelets by Parker et al. (1994b) or in muscle by us. The most parsimonious explanation is that early in sporadic AD the inhibition of neuronal CO activity is caused by a systemic CO defect, rather than by nonspecific hypometabolic conditions following ischemia or other neurodegenerative processes. In this context, the brain would be the most vulnerable organ to show primary pathogenesis as a result of systemic CO inhibition. Neurons are more vulnerable to show CO-dependent pathophysiology than other tissues because the brain is rich in lipids vulnerable to peroxidation and it has higher oxygen consumption, but the brain has less antioxidant defenses than other tissues that are less active aerobically.

EXAMPLE 3

Morphometry of CO-stained Neurons

Overall, the number of CO-stained cell bodies in the IC was variable but relatively small, approximately 35 cell bodies seen per CO-stained section on average, as counted with the optical dissector approach (West, 1993). Microscopic imaging of CO-stained cell bodies revealed high CO activity in the perikaryon (average of 607.7 activity units). Thus, stained cell bodies typically presented themselves as Golgi-like images consisting of a dark perikaryon with a light-colored or clear ovoid or spherical center, which was the unstained mitochondrion-less nucleus of the cell (FIG. 2).

Most of the cells also had variably stained processes which were nearly always determined to be dendritic, since the axon takes little or no stain and is, hence, usually invisible. Some of the processes could occasionally be observed to extend over 100 μm from the soma of the cell.

Figure 1C:
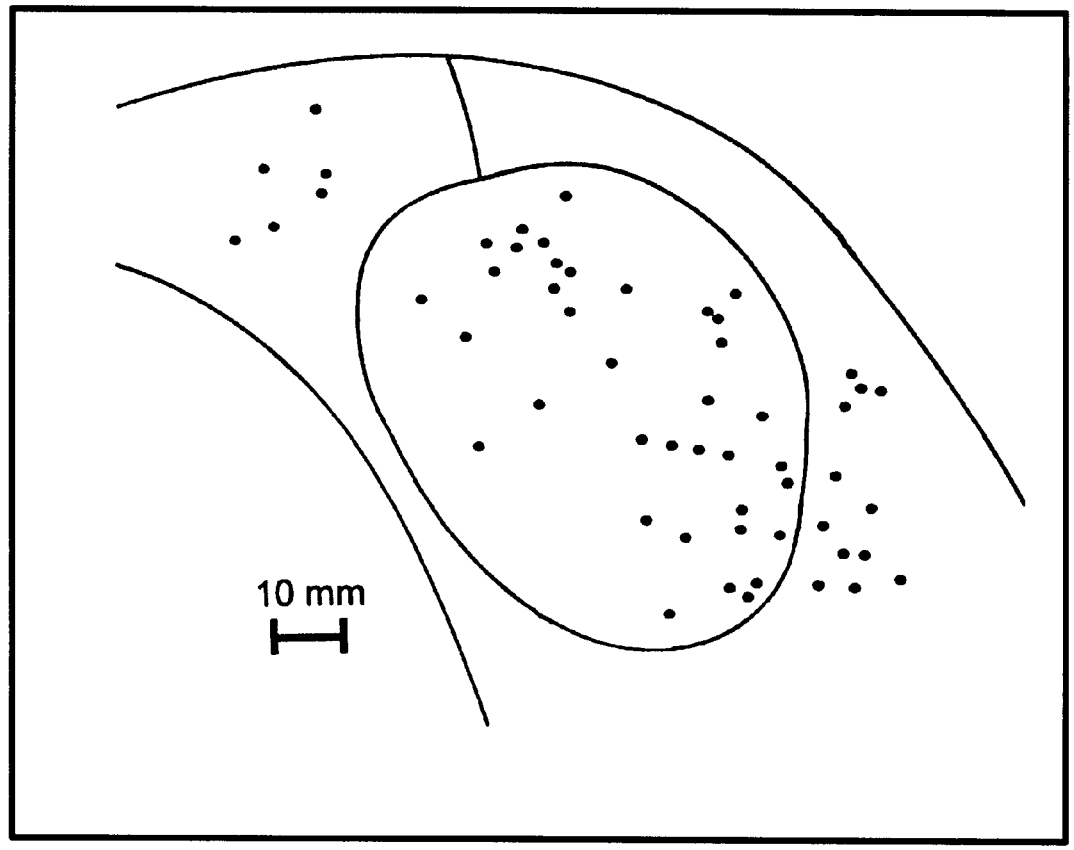
Figure 3A:
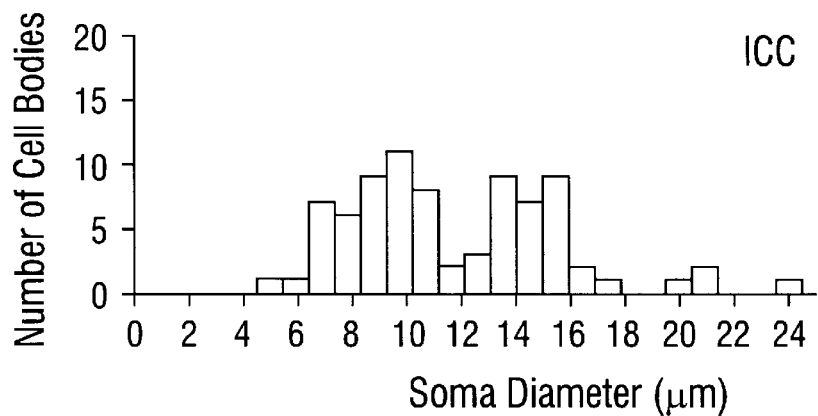
FIG. 3A, FIG. 3B and FIG. 3C. Cell body frequency histograms by soma diameter in each of the three nuclei of the non-AD control group: ICC (FIG. 3A), ICD (FIG. 3B), and ICE (FIG. 3C). Note the bimodal distribution of cell bodies in the ICC; the control and AD groups were subdivided at the mean of the control ICC soma diameters, 12.1 $\mu$m.
Figure 3B:
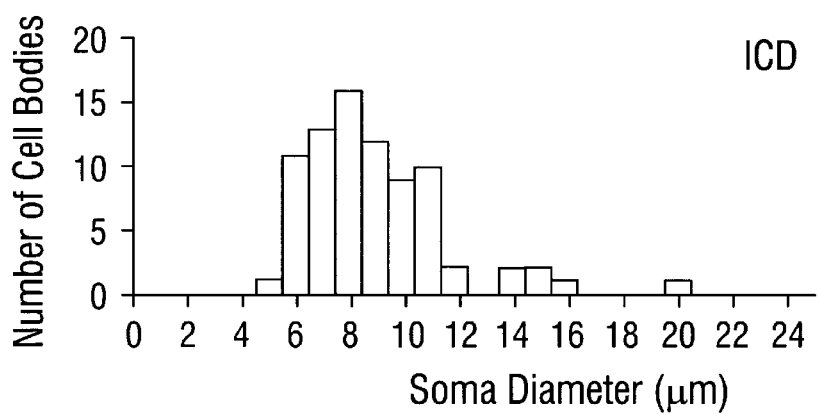
Figure 3C:
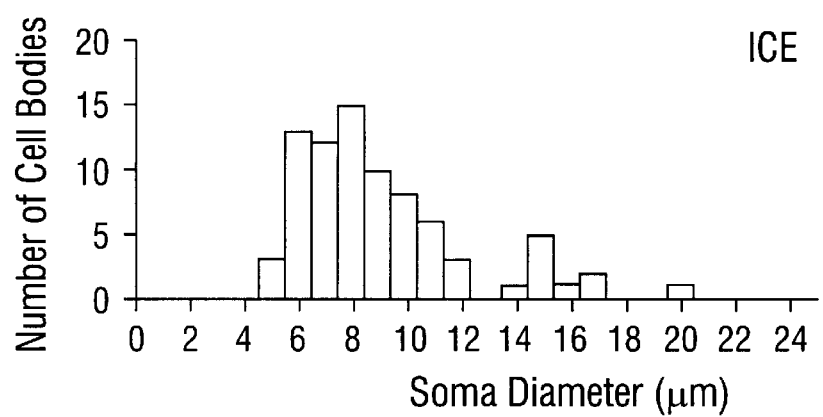

The cellular organization of the IC revealed with CO staining followed closely the descriptions of the cells of the inferior colliculus made by Cajal (1995). The measurements reported here from a sample of 80 cells from each of the three nuclei in the control subjects showed a distribution of the diameters of the sampled cell bodies similar to and approximating Cajal's size categorization. Frequency histograms were constructed for each variable for each IC nucleus in the control group. ICC soma diameter demonstrated a clear bimodal distribution (FIG. 3). Therefore, subsequent comparisons of CO activity variables were also made between larger and smaller cell subgroups classified by the mean of the control group's ICC soma diameter, 12.1 μm. The topographic distribution of the larger cells in the IC is illustrated in FIG. 1C, which shows that they are more abundant in the ICC.

Figure 4A:
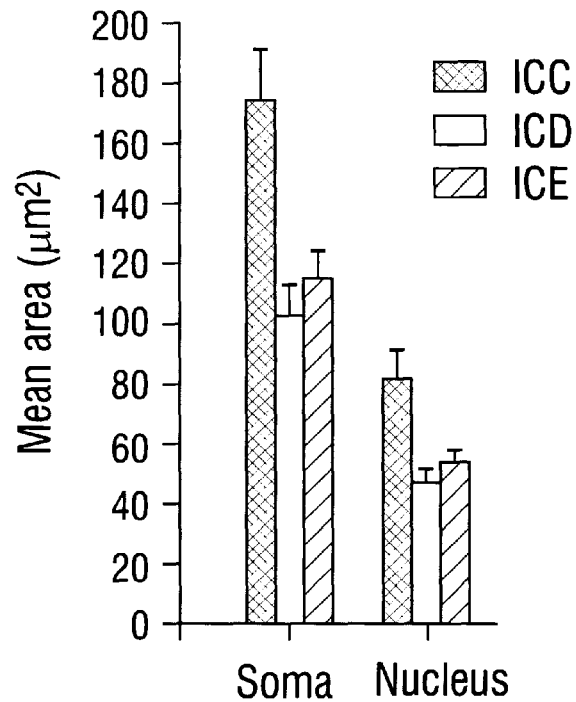
FIG. 4A and FIG. 4B. Comparison between the morphometric measures of areas (FIG. 4A), perimeters and diameters (FIG. 4B) of the three nuclei of the IC within the non-AD control group. The ICC measures were significantly larger than both the ICD and ICE in all morphometric measures ($p<0.05$).
Figure 4B:
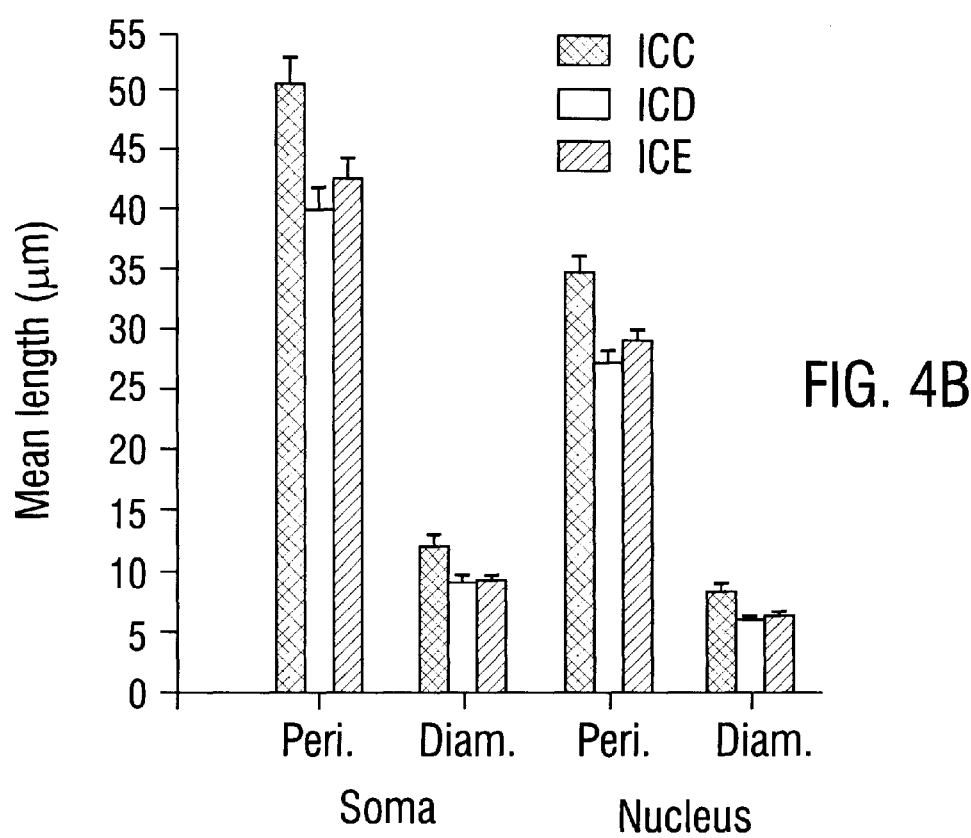

Neuronal soma and nucleus area, perimeter, and diameter were all significantly larger in the ICC as compared to the ICD and ICE (mean±S.E.M. morphometric values are shown in FIG. 4). This is consistent with the observation that the largest overall stained cells were found in the ICC.

The mean soma diameter in the ICD was 8.94±0.61 μm, as compared to 12.09±0.77 in the ICC, with nearly all the cells in the small to medium range and very few large cells. Cajal referred to the ICD as the 'internuclear or dorsal cortex' or 'tectum', and described this region as laminated. However, these laminations are not readily apparent in a CO staining, either under macro- or microimaging conditions.

The mean soma diameter in the ICE measured 9.12±0.45 μm. Cajal termed the ICE as the 'lateral or external cortex' of the inferior colliculus. Most of the cells sampled fell into the small range, with some medium-sized, and few large. Cajal reported a lateral row of small cells. These were approximately 8–10 μm in diameter, with triangular, stellate, or fusiform shapes. A more medial row of medium-sized cells showed neurons somewhat larger, approximately 8–14 μm in diameter, with the majority being triangular and pyramidal shapes, with two or more thick dendrites emanating from the some

EXAMPLE 4

CO Activity in Control Neurons

Figure 5:
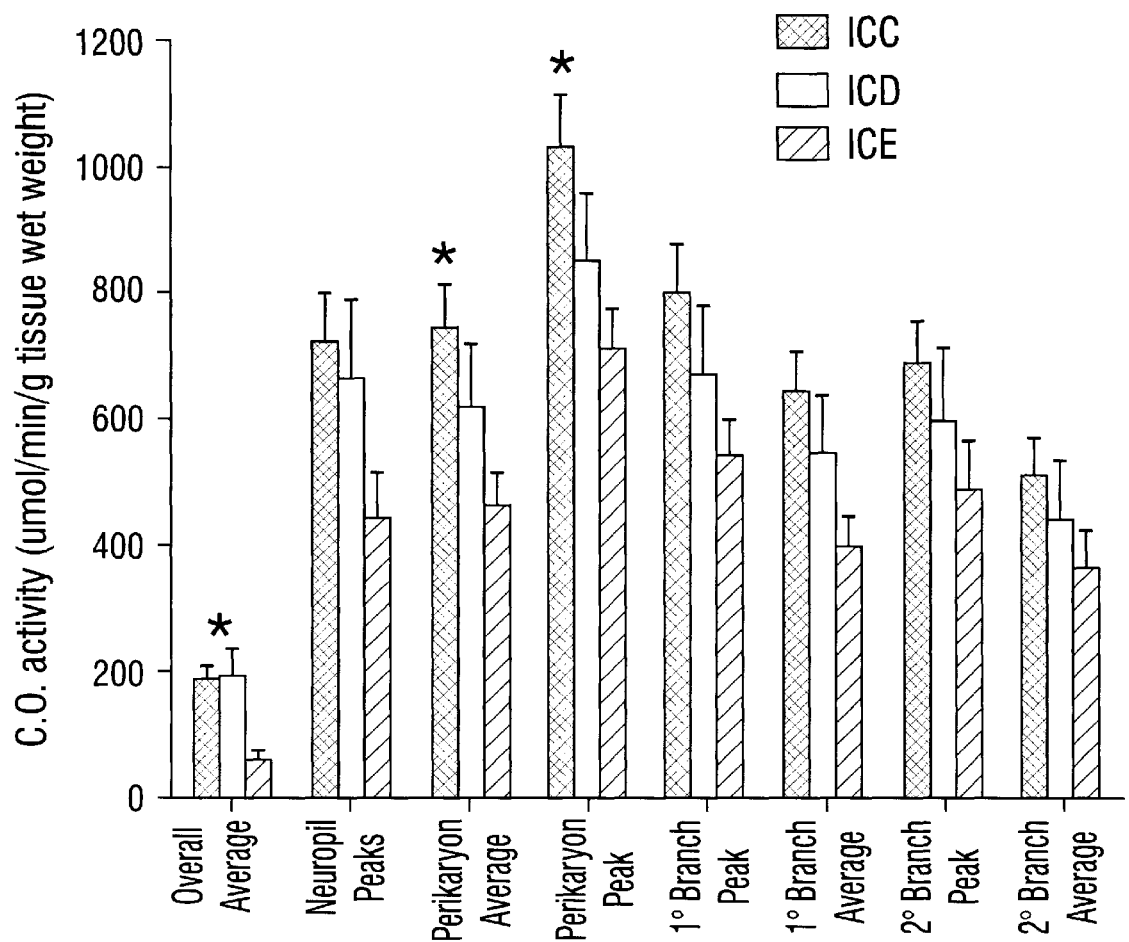
FIG. 5. Comparison between the CO activity measures of the three nuclei of the IC within the non-AD control group. The ICC and ICD differed significantly from the ICE in overall average activity; the ICC alone significantly differed from the ICE in the perikaryon average and peak measures ($p<0.05$).

Mean values of CO activity in the control group are shown in FIG. 5. Each bar represents the mean ±S.E.M. of the 8 non-AD control subjects. The subject score consisted of the mean of the measurements from the 10 cells sampled in each division of the IC. That is, 80 cells per division of the IC, and a total of 240 cells sampled for the three divisions. Comparisons of CO activity between the IC nuclei were made using a one-way analysis of variance with a post-hoc Student-Newman-Keuls test at the 0.05 significance level (SPSS software).

The mean overall average CO activity for cells in both the ICC (183.40±18.77) and ICD (184.98±45.08) was significantly higher than in the ICE (56.46±15.94). It should be noted that the external nucleus merges laterally with the brachium of the IC, and the myelinated fibers projecting from the ICC to the brachium pass through the ICE and may have contributed to this low overall reading. However, the mean comparisons also showed that both the cell perikaryon average and peak activities were significantly higher in the ICE (742.731±67.902 and 1034.065±83.932) relative to the ICE (462.446-4±52.047 and 708.870±64.085).

One-way ANOVA comparisons between the large and small cell subgroups across the entire IC showed that the larger cells (>12.1 μm in diameter) contained higher CO activity as revealed in their perikaryon average ($p<0.001$), perikaryon peak ($p<0.002$), and primary branch peak ($p<0.02$) measures. This is consistent with the view that large cell bodies tend to be of projection neurons supporting greater processes that require higher metabolic demands.

EXAMPLE 5

Comparison with Neurons of AD subjects

Figure 6:
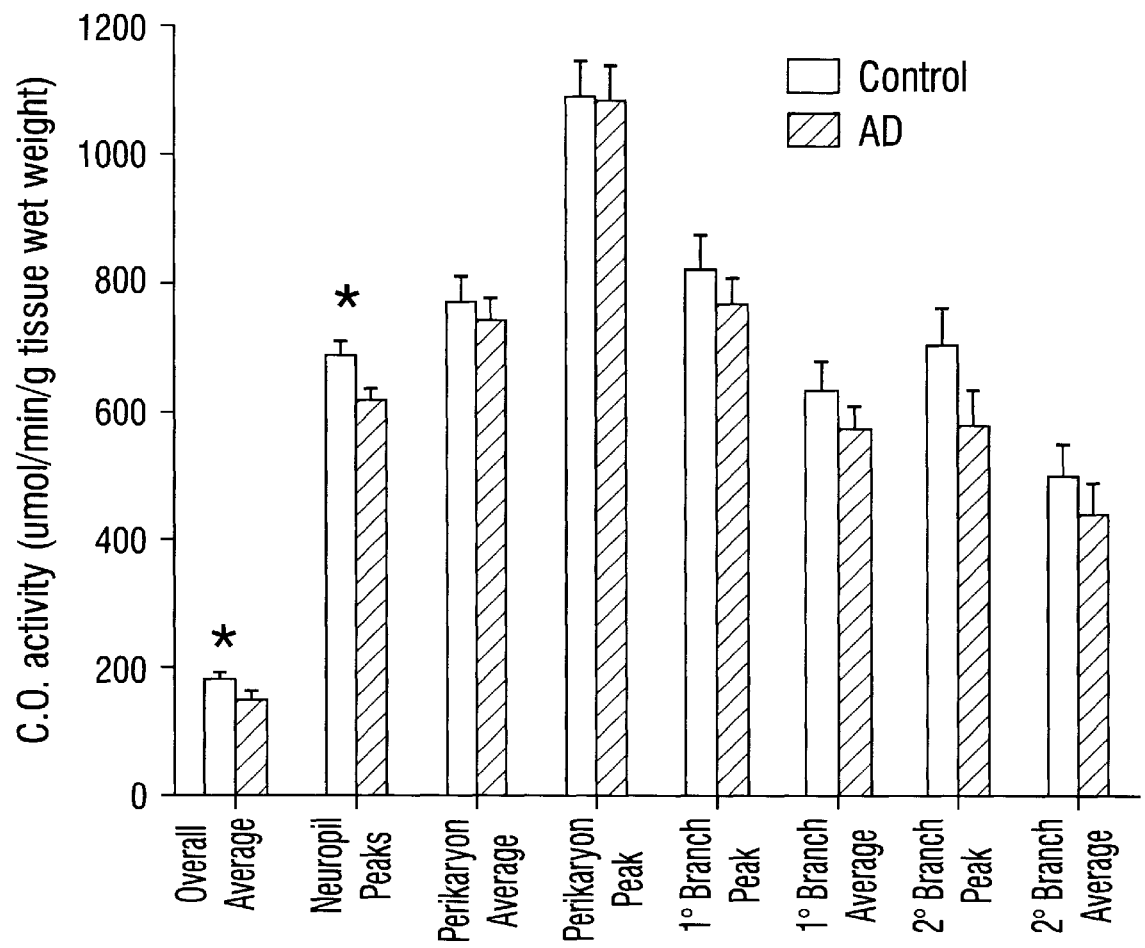
FIG. 6. Comparison of the larger than average cells of the ICC between AD and control. The controls showed significantly more CO activity in the overall average and neuropil peaks measures (*$p<0.05$). This may reflect the heightened vulnerability to AD of the larger projection neurons.

The same morphometric and CO activity measurements done with the 8 controls (n=240 cells) were made with the 8 AD subjects (n=240 cells), matched by age and postmortem time, and the results were compared for each measure. No morphometric differences were found between AD and control measures. The activity measurements from the AD tissue did not differ significantly from the controls when large and small cells were combined in the analysis (one-way ANOVA; SPSS software). However, the large AD cells in the ICC (n=35), as compared to the control cells (n=37), were deficient in CO activity in the overall average ($p<0.032$) and neuropil peaks ($p<0.012$) measures (FIG. 6). This corresponded to a 17.7% decrement in overall average activity and a 10.3% decrement in peak neuropil activity. No significant activity differences were found in the small cell subgroup.

EXAMPLE 6

Methodological Validation of Quantitative CO Cytochemistry

Peripheral and brain tissues from rats and humans were stained with the CO technique of the present invention (FIG. 8A–FIG. 8H).

Figure 9:
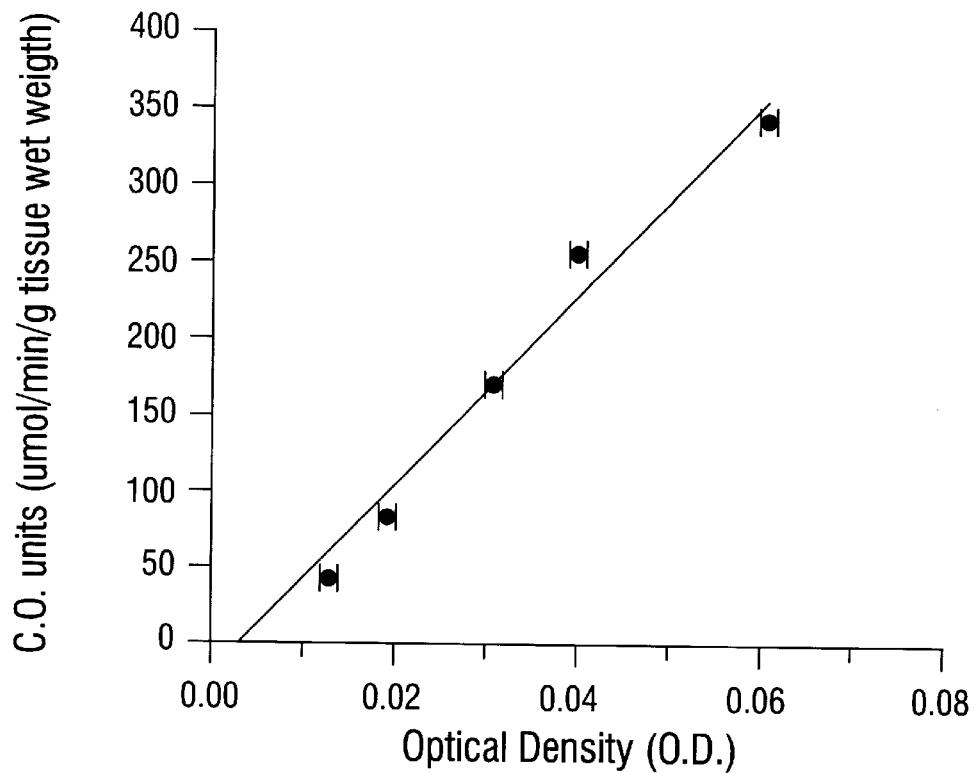
FIG. 9. Calibration curve showing the linear relationship between CO activity and optical density in the cytochemical tissue standards. Activity units were measured spectrophotometrically and are expressed as $\mu$mol/min/g tissue wet weight. Optical density of both brain and peripheral tissue standards was measured with an imaging system calibrated with an optical density step tablet. Standard error bars of mean measures are shown, but in most cases are smaller than the size of the symbols.

For the validation of activity standards, samples of each standard were assayed for calculation of specific activity spectrophotometrically. Percent weight of standards was related to assessed activity. The relationships between time of incubation, section thickness, and activity of dissected regions, with their reaction product measured densitometrically were demonstrated. After systematically varying parameters for the assays, peripheral tissue and brain standards were developed which showed a linear relationship ($r=0.999$) between CO activity (activity units) and CO reactivity (O.D. units) (FIG. 9).

Figure 10:
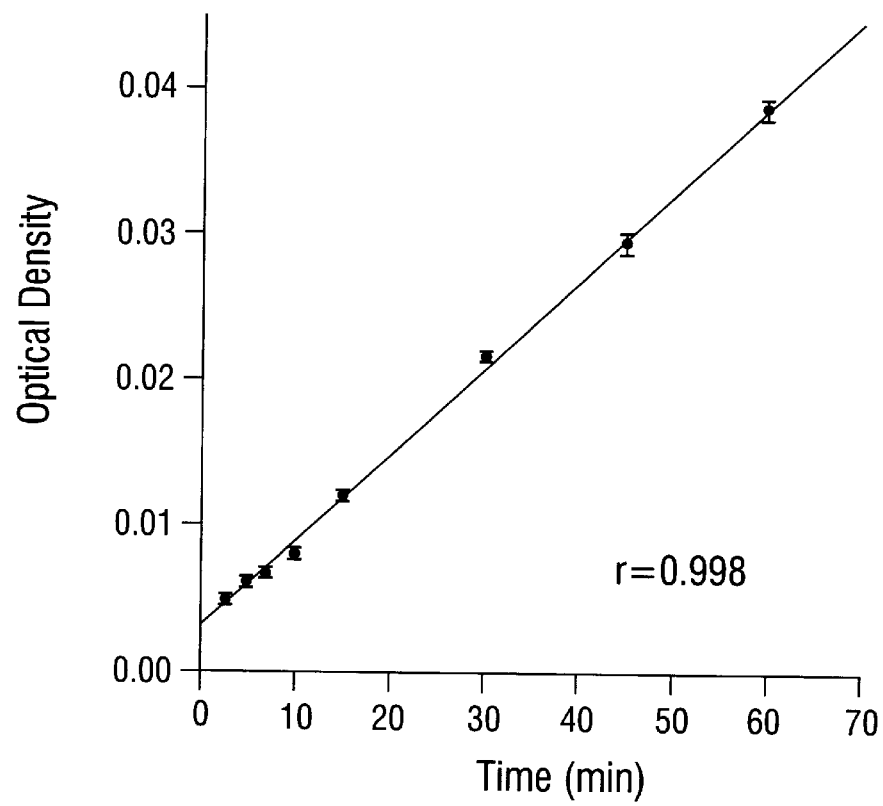
FIG. 10. Effect of cytochemical incubation time on optical density of 40 $\mu$m brain sections. The increase in optical density was linear with respect to increasing time in the 37° C. incubation medium. Standard error bars of mean measures are shown, but in most cases are smaller than the size of the symbols.
Figure 11:
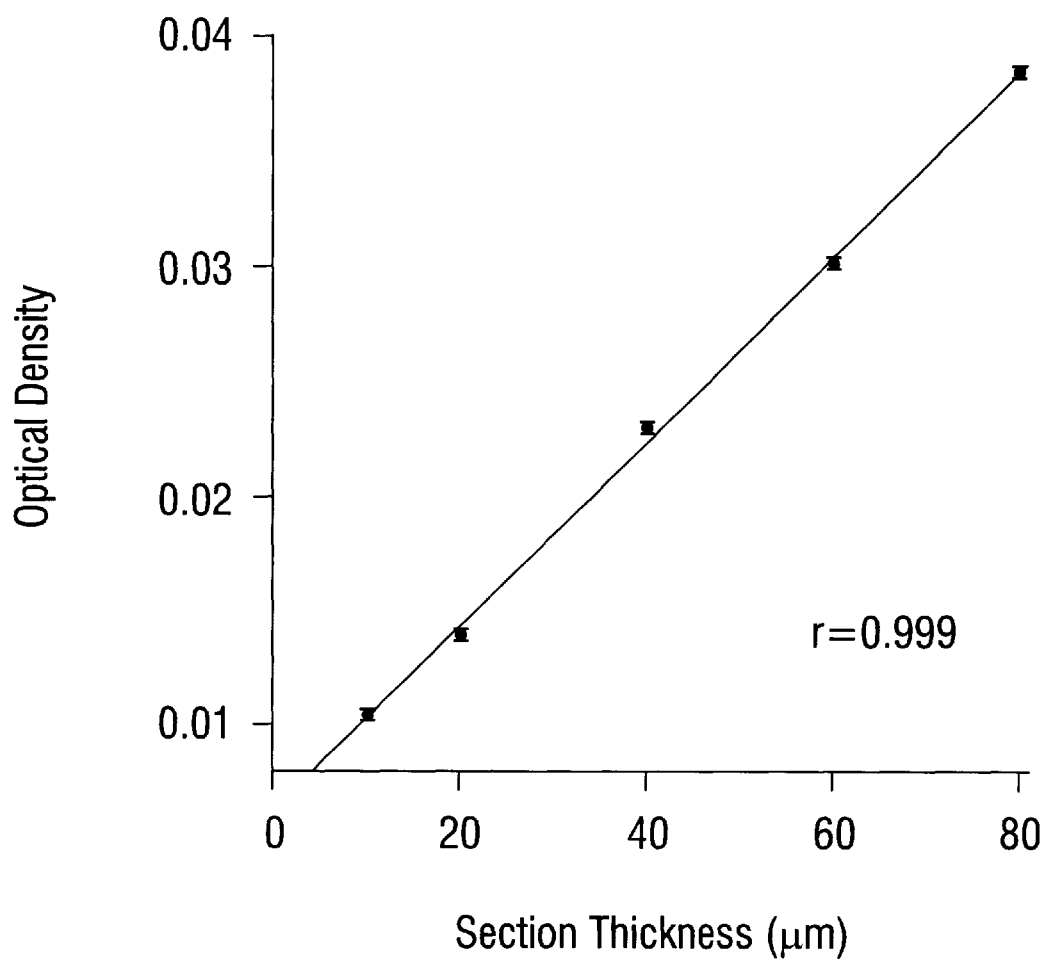
FIG. 11. Effect of section thickness on optical density of standard brain homogenate sections incubated for 60 min at 37° C. The increasing optical density was linear with respect to increased section thickness of the paste standards. Standard error bars of mean optical density are shown, but in most cases are smaller than the size of the symbols.

Heart ventricular muscle was used because it is the tissue with the highest CO activity. A rat brain homogenate did not exhibit as much CO activity as the most active regions of the brain including auditory nuclei. Therefore, when using standards with less activity than whole-brain homogenates, it is necessary to extrapolate CO activity units above the range of observations made to include the brain structures with the most activity. Brain homogenate standards cut in increasing thicknesses served to obtain increasing proportions of CO reactivity. This was the most convenient method when used with the CO cytochemical procedure described above because it resulted in a rate of reaction linear with respect to increasing incubation time (FIG. 10) and section thickness (FIG. 11).

The calibration procedure for the conversion of densitometric measures of reaction product (O.D.) to spectrophotometric measures of enzyme activity units was further verified by comparison of dissected brain regions analyzed spectrophotometrically with the converted units obtained in stained tissue sections. The measured activity units were linearly correlated ($r=0.96$) with the O.D. of histochemical stain (Gonzalez-Lima and Jones, 1994), similar to the findings with the tissue standards.

The quantitative cytochemical method as proposed here provides a good indicator of fresh tissue CO enzymatic activity (i.e., without a substantial fixation inhibition) because preincubation fixation is limited to 5 min with 0.5% glutaraldehyde. The inventor has directly assessed the effect of this preincubation fixation step by comparing adjacent sections from the same tissue standards that either remained totally unfixed (n=14) or that were fixed with 0.5% glutaraldehyde for 5 min (n=14). All sections were stained together on the same baths side-by-side. The mean O.D. units of the unfixed sections (10 readings/section) was 0.039 (+0.002 standard deviation), while the mean for the fixed sections was 0.038 (+0.002 standard deviation). This difference (2.52%) was not statistically significant ($p=0.30$, $t=1.07$, $df=13$). It was determined that only a very small decrease in CO reactivity was produced by the brief fixation step before the preincubation and incubation baths. This step is done only to affix the sections onto the slides to prevent sections from floating off during subsequent staining baths.

The present CO cytochemical procedure demonstrated that it fulfills general quantitative methodological requirements detailed by Stoward (1980). First, there needs to be a way to subtract any nonspecific staining. This was done in the present method by image subtraction of the O.D. background of unreactive tissue standards. Second, the change in O.D. must be linear during the incubation period (FIG. 10). Third, the enzyme activity must increase in proportion to tissue section thickness (FIG. 11). Finally, there needs to be a conversion procedure (FIG. 9) by comparison of data measured biochemically to provide a way to express measures in O.D. as actual enzyme units. The validity of the conversion procedure was verified also using dissected brain regions. The method presented here fulfilled these quantitative criteria and thus provides a superior approach for regional mapping studies of CO activity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Adams, J. C., "Technical considerations on the use of horseradish peroxidase as a neuronal marker", *Neurosci.*, 2:141–145, 1977.

Akaaboune et al., "Apolipoprotein E expression at neuromuscular junctions in mouse, rat and human skeletal muscle, FEBS Letters, 351, 246–248, 1994.

Bauserman et al., "Mitochondrial myopathies", In Heffner, R. R. (Ed.), Muscle Pathology, L. W. Roth, Series Ed., Churchill-Livingstone, Inc., New York., 1984.

Bennett et al., "Cytochrome oxidase inhibition: a novel animal model of Alzheimer's disease", *Journal of Geriatric Psychiatry & Neurology*, 5:93–101, 1992.

Benzi et al., "Effect of chronic treatment with some drugs on the enzymatic activities of the rat brain", *Biochem. Pharmacol.*, 28:2703–2708, 1979.

Cada et al., "Regional brain effects of sodium azide treatment on cytochrome oxidase activity: A quantitative histochemical study", *Metabolic Brain Disease*, 10:303–320, 1995.

Cajal, Ramon y, *In: Histology of the Nervous System of Man and Vertebrates*, Translated by N. Swanson and L. W. Swanson, Oxford University Press, New York, 125–142, 1995.

Chieco et al., "A user's guide for avoiding errors in absorbance image cytometry: a review with original experimental observations", *Histochem. J.*, 26:1–19, 1994.

Curti et al., "Age-related modifications of cytochrome c oxidase activity in discrete brain regions", *Mech. Ageing and Dev.*, 55:171–180, 1990.

Darriet et al., "Distribution of cytochrome oxidase in rat brain: studies with diaminobenzidine histochemistry in vitro and [14C]cyanide tissue labeling in vivo", *J. Cereb. Blood Flow Metab.*, 6:8–14, 1986.

Davis et al., "Mutations in mitochondrial cytochrome c oxidase genes segregate with late-onset Alzheimer's disease", *Proc. Nat'l Acad Sci.*, 94:4526–4531, 1997.

de la Monte et al., "Increased levels of neuronal thread protein in cerebrospinal fluid of patients with Alzheimer's disease", *Annals of Neurology*, 32:733–742, 1992.

De Olmos and Heimer, "Mapping of collateral projections with the HRP-method", *Neurosci. Lett.*, 6:107–114, 1977.

Gonzalez-Lima and Cada, "Cytochrome oxidase activity in the auditory system of the mouse: A qualitative and quantitative histochemical study", A *Neuroscience*, 63:559–578, 1994.

Gonzalez-Lima and Garrosa, "Quantitative histochemistry of cytochrome oxidase in rat brain", *Neuroscience Letters*, 123:251–253, 1991.

Gonzalez-Lima and Gonzalez-Lima, "Sources of stress affecting caregivers of Alzheimer's disease patients", *Health Values*, 11, 3–10, 1987.

Gonzalez-Lima and Jones, "Quantitative mapping of cytochrome oxidase activity in the central auditory system of the gerbil: A study with calibrated activity standards and metal-intensified histochemistry", *Brain Res.*, 660:34–49, 1994.

Gonzalez-Lima et al., "Functional mapping of the rat brain during drinking behavior: A fluorodeoxyglucose study", *Physiol. and Beh*, 54:605–612, 1993.

Gonzalez-Lima et al., "Quantitative cytochemistry of cytochrome oxidase and cellular morphometry of the human inferior colliculus in control and Alzheimer's patients", *Brain Res.*, 752:117–126, 1997.

Gonzalez-Lima and Scheich, "Functional activation in the auditory system of the rat produced by arousing reticular stimulation: A 2-deoxyglucose study", *Brain Res.* 299:201–214, 1984.

Gonzalez-Lima, F., "Brain imaging of auditory learning functions in rats: Studies with fluorodeoxyglucose autoradiography and cytochrome oxidase histochemistry", In: Gonzalez-Lima, F., Finkenstaedt, Th., and Scheich, H. (eds.), Advances in Metabolic Mapping Techniques for Brain Imaging of Behavioral and Learning Functions, Kluwer Academic Publishers, Dordrecht/Boston/London NATO ASI Series D, Vol. 68: pp 39–109, 1992.

Hess and Pope, "Ultramicrospectrophotometric determination of cytochrome oxidase for quantitative histochemistry", *J. Biol. Chem.*, 204:295–306, 1953.

Hevner et al., "An optimized method for determining cytochrome oxidase activity in brain tissue homogenates", *J. of Neuroscience Methods*, 50:309–319, 1993.

Jones et al., "Effects of intrauterine position on the metabolic capacity of the hypothalamus of female gerbils", *Physiol. Behav.* 61:513–519, 1997.

Kageyama and Robertson, "Relationships between neuromorphogenesis and cytochrome oxidase (CO) activity in rat auditory and visual cortices, hippocampus and cerebellum as demonstrated with metal-intensified CO histochemistry", *Soc. Neurosci. Abstr.*, 19:1711, 1993.

Kugler et al., "Cytochrome oxidase histochemistry in the rat hippocampus: A quantitative methodological study", *Histochem.*, 89:269–275, 1988.

Liu et al., "An improved staining technique for cytochrome C oxidase", *J. Neurosci. Meth.* 49:181–184, 1993.

Lowry et al., "Protein measurement with the Folin phenol reagent", *J. Biol. Chem.*, 193:295–275, 1951.

Mecocci et al., "Oxidative damage to mitochondrial DNA is increased in Alzheimer's disease", *Annals of Neurology*, 36:747–751, 1994.

Nobrega, J. N., "Brain metabolic mapping and behaviour: Assessing the effects of early developmental experiences in adult animals", In Gonzalez-Lima, F., Findenstaedt, T., and Scheich, H. (eds.), Advances in Metabolic Mapping Techniques for Brain Imaging of Behavioral and Learning Functions, Kluwer Academic Publishers, Dordrecht/Boston/London, NATO ASI Series D, Vol. 68: pp. 125–149, 1992.

Nobrega, N., "Long-term changes in regional brain cytochrome oxidase activity induced by electroconvulsive treatment in rats", *Brain Res.*, 605:1–8, 1993.

Parker and Parks, "Cytochrome c oxidase in Alzheimer's disease brain: purification and characterization", *Neurology* 45(3)482–486, 1995.

Parker et al., "Cytochrome oxidase deficiency in Alzheimer's Disease", *Neurology*, 40:1302–1303, 1990.

Parker et al., "Electron transport chain defects in AD brain", *Neurology*, 44:1090–1096, 1994b.

Parker et al., "Reduced platelet cytochrome c oxidase activity in AD", *Neurology*, 44:1086–1090, 1994a.

Sarnat, H. B., "Muscle Pathology and Histochemistry", Chicago American Society of Clinical Pathologists Press, 1983.

Schagger and Ohm, "Human diseases with effects in oxidative phosphorylation. 2. F1F0 ATP-synthase defects in Alzheimer disease revealed by blue native polyacrylamide gel electrophoresis, *Eur J Biochem*, 227(3):916–21, 1995.

Seligman et al., "Nondroplet ultrastructural demonstration of cytochrome oxidase activity with a polymerizing osmiophilic reagent, diaminobenzidine (DAB)", *J. of Cell Biol.*, 38:1–14, 1968.

Silverman and Tootell, "Modified technique for cytochrome oxidase histochemistry: Increased staining intensity and compatibility with 2-deoxyglucose autoradiography", *J. Neurosci. Meth.*, 19:1–10., 1987.

Sokoloff, L., "Circulation and energy metabolism of the brain" In G. J. Siegel, B. W. Agranoff, R. W. Albers, & P. Molinoff (Eds.), Basic Neurochemistry, pp. 471–495, Boston: Little Brown, 1989.

Stoward, "Criteria for the validation of quantitative histochemical enzyme techniques," In: Trends in Enzyme Histochemistry and Cytochemisty, Ciba Foundation, Excerpta Medica, Amsterdam, pp. 11–31, 1980.

U.S. Pat. No. 5,545,566

U.S. Pat. No. 5,686,269

U.S. Pat. No. 5,705,401

Van Raamsdonk et al., "Quantitative cytochemical analysis of cytochrome oxidase and succinate dehydrogenase activity in spinal neurons", Acta Histochem., 81:129–141, 1987.

Van Zuylen et al., "No evidence for reduced thrombocyte cytochrome oxidase activity in Alzheimer's Disease", Neurology, 42:1246–1247, 1992.

West, "New stereological methods for counting neurons", Neurobiol. Aging, 14:275–285, 1993.

Wharton and Tzagoloff, "Cytochrome oxidase from beef heart mitochondria", Methods of Enzymology, 10:245–250, 1967.

Wong-Riley, "Cytochrome oxidase: an endogenous metabolic marker for neuronal activity", Trends in Neurosciences, 12:94–101, 1989.

Wong-Riley, M. T. T., "Changes in monocularly sutured or enucleated cats demonstrable with cytochrome oxidase histochemistry", Brain Res., 171:11–28, 1979.

What is claimed is:

1. A method of diagnosing late-onset sporadic Alzheimer's Disease (AD) comprising the steps of:

(a) obtaining a sample from a human subject;

(b) assessing cytochrome oxidase activity in nucleated cells of said sample; and (c) comparing the cytochrome oxidase activity in nucleated cells of said sample with the cytochrome oxidase activity of a standard, wherein a decrease in cytochrome oxidase activity in nucleated cells of said sample, with respect to said standard, indicates that said subject has AD.

2. The method of claim 1, wherein said standard is cytochrome oxidase activity of nucleated cells of the same tissue type as the sample from an individual not afflicted with AD.

3. The method of claim 2, wherein said method further comprises assessing cytochrome oxidase activity from said nucleated cells of the same tissue type as the sample from an individual not afflicted with AD.

4. The method of claim 1, wherein said sample is a superficial tissue biopsy.

5. The method of claim 4, wherein said biopsy is from a tissue selected from the group consisting of muscle, dermis, epidermis, bone marrow, peripheral ganglion or nerve.

6. The method of claim 1, wherein said assessing comprises providing diaminobenzidine (DAB) to cells of said sample and measuring oxidation of DAB to an indamine polymer.

7. The method of claim 6, wherein measuring oxidation of DAB to an indamine polymer comprises quantitative cytochemistry when calibrated with spectrophotometry.

8. The method of claim 1, wherein said sample is frozen and sectioned.

9. The method of claim 1, wherein cytochrome oxidase activity is quantified.

10. The method of claim 1, wherein the cytochrome oxidase activity level of cells of said sample is 15% or more below the cytochrome oxidase activity level of said nucleated cells of the same tissue type as the sample from an individual not afflicted with AD.

11. A method for monitoring a treatment for late-onset sporadic AD comprising the steps of:

(a) obtaining a sample from a human subject following a treatment thereof;

(b) assessing cytochrome oxidase activity in nucleated cells of said sample; and (c) comparing the cytochrome oxidase activity in nucleated cells of said sample with a standard;

wherein an increase in cytochrome oxidase activity in nucleated cells of said sample, with respect to said standard, indicates that said treatment is effective.

12. The method of claim 11, wherein said standard is cytochrome oxidase activity of nucleated cells of the same tissue type as the sample from said subject prior to said treatment.

13. The method of claim 11, wherein said standard is cytochrome oxidase activity of said nucleated cells of the same tissue type as the sample from an individual not afflicted with AD.

14. The method of claim 11, wherein said sample is a superficial tissue biopsy.

15. The method of claim 11, wherein said assessing comprises providing diaminobenzidine (DAB) to cells of said sample and measuring oxidation of DAB to an indamine polymer.

16. The method of claim 15, wherein measuring oxidation of DAB to an indamine polymer comprises quantitative cytochemistry when calibrated with spectrophotometry.

17. The method of claim 11, wherein said sample is frozen and sectioned.

18. A diagnostic kit comprising:

(a) a cytochrome oxidase substrate in a suitable container means therefor;

(b) a cytochrome oxidase enzyme preparation for use as a standard, and a suitable container means therefor.

19. A kit of claim 18, wherein said substrate is diaminobenzidine.

20. A kit of claim 18, further comprising reagents for preparation of histological samples.

* * * * *

UNITED STATES PATENT AND TRADEMARK OFFICE
CERTIFICATE OF CORRECTION

PATENT NO. : 6,183,981 B1
APPLICATION NO. : 09/262699
DATED : February 6, 2001
INVENTOR(S) : Francisco Gonzales-Lima It is certified that error appears in the above-identified patent and that said Letters Patent is hereby corrected as shown below:

IN THE SPECIFICATIONS:
In column 1, lines 8-11, delete "The government may own rights in the present invention pursuant to grant number RO1 MH43353 from the National Institutes of Health and grant number 003658-361 from the Advanced Technology Program, State of Texas" and insert
--This invention was made with government support under grant number RO1 MH43353, awarded by the National Institutes of Health, and grant number 003658-361 awarded by the Advanced Technology Program, State of Texas. The government has certain rights in the invention.-- therefor.

Signed and Sealed this
Tenth Day of May, 2011

David J. Kappos
*Director of the United States Patent and Trademark Office*